(12) United States Patent
Duan

(10) Patent No.: US 9,567,586 B2
(45) Date of Patent: Feb. 14, 2017

(54) EPCAM APTAMER FOR DETECTION OF CANCER STEM CELLS

(71) Applicant: DEAKIN UNIVERSITY, Victoria (AU)

(72) Inventor: Wei Duan, Victoria (AU)

(73) Assignee: Deakin University, Waurn Ponds, Victoria (AU)

(*) Notice: Subject to any disclaimer, the term of this patent is extended or adjusted under 35 U.S.C. 154(b) by 0 days.

(21) Appl. No.: 14/418,660

(22) PCT Filed: Aug. 2, 2013

(86) PCT No.: PCT/AU2013/000851
§ 371 (c)(1),
(2) Date: Jan. 30, 2015

(87) PCT Pub. No.: WO2014/019025
PCT Pub. Date: Feb. 6, 2014

(65) Prior Publication Data
US 2015/0197755 A1 Jul. 16, 2015

(30) Foreign Application Priority Data

Aug. 2, 2012 (AU) ................................ 2012903333

(51) Int. Cl.
| | | |
|---|---|---|
| *C07H 21/04* | (2006.01) | |
| *C12N 15/113* | (2010.01) | |
| *C12N 15/115* | (2010.01) | |
| *A61K 47/48* | (2006.01) | |
| *A61K 49/00* | (2006.01) | |
| *A61K 51/04* | (2006.01) | |
| *A61K 31/713* | (2006.01) | |
| *G01N 33/574* | (2006.01) | |
| *G01N 33/53* | (2006.01) | |

(52) U.S. Cl.
CPC ......... *C12N 15/1138* (2013.01); *A61K 31/713* (2013.01); *A61K 47/48092* (2013.01); *A61K 49/0002* (2013.01); *A61K 51/0491* (2013.01); *C12N 15/113* (2013.01); *C12N 15/115* (2013.01); *G01N 33/5308* (2013.01); *G01N 33/574* (2013.01); *G01N 33/57407* (2013.01); *G01N 33/57492* (2013.01); *C12N 2310/14* (2013.01); *C12N 2310/16* (2013.01); *C12N 2310/351* (2013.01); *C12N 2310/3519* (2013.01); *C12N 2320/31* (2013.01); *G01N 2333/70503* (2013.01)

(58) Field of Classification Search
CPC ...................................................... C07H 21/04
See application file for complete search history.

(56) References Cited

FOREIGN PATENT DOCUMENTS

| WO | 2010/023327 A2 | 3/2010 |
|---|---|---|
| WO | 2013/003898 A1 | 1/2013 |

OTHER PUBLICATIONS

Kanwar et al. (Critical Reviews in Bio and Mol Biology 2011: 459-477).*
Australian Patent Office, "International Search Report for PCT/AU2013/000851", Sep. 3, 2013, 5 pages.
Australian Patent Office, "Written Opinion for PCT/AU2013/000851", Sep. 3, 2013, 7 pages.
Cerchia, Laura et al., "Nucleic acid aptamers in cancer medicine", FEBS Letters, vol. 528, 2002, 12-16.
Shigdar, S. et al., "RNA aptamer against a cancer stem cell marker epithelial cell adhesion molecule", Cancer Science, vol. 102, No. 5, 2011, 991-998.
Cibiel, et al., "Methods to Identify Aptamers against Cell Surface Biomarkers", Pharmaceuticals, vol. 4, No. 9, pp. 1216-1235, XP055019301, DOI: 10.3390/ph4091216, Sep. 20, 2011, 20 Pages.
Imrich, et al., "EpCAM and its potential role in tumor-initiating cells", Cell Adhesion and Migration, vol. 6, No. 1, pp. 30-38, XP055245944, us ISSN: 1933-6918, DOI: 10.4161/cam.18953, Jan. 1, 2012, 10 Pages.
Shigdar, et al., "Supporting Information: RNA aptamer against a cancer stem cell marker epithelial cell adhesion molecule", Cancer Science, pp. 1-5, XP055246000, DOI: 10.1111/j.1349-7006.2011.01897, Retrieved from the Internet: URL:http://onlinelibrary.wiley.com/doi/10. 1111/j.1349-7006.2011.01897.x/suppinfo [Retrieved on Jan. 29, 2016], Mar. 14, 2011, 6 Pages.
European Patent Office, "Extended European Search Report dated Feb. 10, 2016 for European Patent Application No. 13825695.3", Feb. 10, 2016, 6 Pages.

* cited by examiner

*Primary Examiner* — Kimberly Chong
(74) *Attorney, Agent, or Firm* — Dorsey & Whitney LLP

(57) ABSTRACT

The present disclosure relates to an RNA aptamer and uses thereof, in particular, an aptamer which specifically bind to EpCAM and which demonstrates superior tumor penetrating ability.

24 Claims, 18 Drawing Sheets

(A)

(B)

(C)

(D)

A

B

SEQUENCE LISTING

<160> NUMBER OF SEQ ID NOS: 13

<210> SEQ ID NO 1
<211> LENGTH: 19
<212> TYPE: RNA

```
<213> ORGANISM: Artificial Sequence
<220> FEATURE:
<223> OTHER INFORMATION: chemically synthesized sequence

<400> SEQUENCE: 1
gcgacugguu acccggucg                                                    19

<210> SEQ ID NO 2
<211> LENGTH: 19
<212> TYPE: RNA
<213> ORGANISM: Artificial Sequence
<220> FEATURE:
<223> OTHER INFORMATION: chemically synthesized sequence

<400> SEQUENCE: 2
acguaucccu uuucgcgua                                                    19

<210> SEQ ID NO 3
<211> LENGTH: 43
<212> TYPE: RNA
<213> ORGANISM: Artificial Sequence
<220> FEATURE:
<223> OTHER INFORMATION: chemically synthesized sequence

<400> SEQUENCE: 3
acguaucccu uuucgcguaa aauguagaga ugcggugguc cuu                         43

<210> SEQ ID NO 4
<211> LENGTH: 15
<212> TYPE: RNA
<213> ORGANISM: Artificial sequence
<220> FEATURE:
<223> OTHER INFORMATION: chemically synthesized sequence

<400> SEQUENCE: 4
cccuccuaca uaggg                                                        15

<210> SEQ ID NO 5
<211> LENGTH: 19
<212> TYPE: RNA
<213> ORGANISM: Artificial Sequence
<220> FEATURE:
<223> OTHER INFORMATION: chemically synthesized sequence

<400> SEQUENCE: 5
cagaacguau acuauucug                                                    19

<210> SEQ ID NO 6
<211> LENGTH: 60
<212> TYPE: DNA
<213> ORGANISM: Artificial Sequence
<220> FEATURE:
<223> OTHER INFORMATION: sense oligonucleotide

<400> SEQUENCE: 6
taatacgact cactataggt ccgtagttct ggctgactgg ttacccggtc gtacagctcg       60

<210> SEQ ID NO 7
<211> LENGTH: 60
<212> TYPE: DNA
<213> ORGANISM: Artificial Sequence
<220> FEATURE:
<223> OTHER INFORMATION: antisense oligonucleotide

<400> SEQUENCE: 7
cgagctgtac gaccgggtaa ccagtcagcc agaactacgg acctatagtg agtcgtatta      60
```

<210> SEQ ID NO 8
<211> LENGTH: 36
<212> TYPE: DNA
<213> ORGANISM: Artificial Sequence
<220> FEATURE:
<223> OTHER INFORMATION: sense oligonucleotide

<400> SEQUENCE: 8
taatacgact cactatagcg actggttacc cggtcg                               36

<210> SEQ ID NO 9
<211> LENGTH: 36
<212> TYPE: DNA
<213> ORGANISM: Artificial Sequence
<220> FEATURE:
<223> OTHER INFORMATION: antisense oligonucleotide

<400> SEQUENCE: 9
cgaccgggta accagtcgct atagtgagtc gtatta                               36

<210> SEQ ID NO 10
<211> LENGTH: 36
<212> TYPE: DNA
<213> ORGANISM: Artificial Sequence
<220> FEATURE:
<223> OTHER INFORMATION: sense oligonucleotide

<400> SEQUENCE: 10
taatacgact cactataacg tatccctttt cgcgta                               36

<210> SEQ ID NO 11
<211> LENGTH: 19
<212> TYPE: DNA
<213> ORGANISM: Artificial Sequence
<220> FEATURE:
<223> OTHER INFORMATION: antisense oligonucleotide

<400> SEQUENCE: 11
tacgcgaaaa gggatacgt                                                  19

<210> SEQ ID NO 12
<211> LENGTH: 20
<212> TYPE: RNA
<213> ORGANISM: Artificial Sequence
<220> FEATURE:
<223> OTHER INFORMATION: chemically synthesized sequence
<220> FEATURE:
<221> NAME/KEY: misc_feature
<222> LOCATION: (20)..(20)
<223> OTHER INFORMATION: n= inverted deoxythymidine

<400> SEQUENCE: 12
gcgacugguu acccggucgn                                                 20

<210> SEQ ID NO 13
<211> LENGTH: 20
<212> TYPE: RNA
<213> ORGANISM: Artificial Sequence
<220> FEATURE:
<223> OTHER INFORMATION: chemically synthesized sequence
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (3)..(3)

```
<223> OTHER INFORMATION: gm
<220> FEATURE:
<221> NAME/KEY: modified_base
<222> LOCATION: (7)..(7)
<223> OTHER INFORMATION: gm
<220> FEATURE:
<221> NAME/KEY: modified_base
<222> LOCATION: (8)..(8)
<223> OTHER INFORMATION: gm
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (16)..(16)
<223> OTHER INFORMATION: gm
<220> FEATURE:
<221> NAME/KEY: misc_feature
<222> LOCATION: (20)..(20)
<223> OTHER INFORMATION: n= inverted deoxy thymidine

<400> SEQUENCE: 13
gcgacugguu acccggucgn                                            20
```

EPCAM APTAMER FOR DETECTION OF CANCER STEM CELLS

CROSS-REFERENCE TO RELATED APPLICATIONS

The present application is a Section 371 National Stage Application of International Application No. PCT/AU2013/000851, filed on Aug. 2, 2013, which claims priority to Australian Application No. 2012903333, filed on Aug. 2, 2012, both of which are hereby incorporated by reference in their entirety.

SEQUENCE LISTING

A sequence listing submitted in computer readable format is hereby incorporated by reference. The computer readable file is named P516233WOUS01_ST25.txt and contains 4.0 kilobytes.

RELATED APPLICATIONS AND INCORPORATION BY REFERENCE

All documents cited or referenced herein, and all documents cited or referenced in herein cited documents, together with any manufacturer's instructions, descriptions, product specifications, and product sheets for any products mentioned herein or in any document incorporated by reference herein, are hereby incorporated herein by reference in their entirety.

FIELD OF THE INVENTION

The present disclosure relates to an RNA aptamer and uses thereof, in particular, an aptamer which specifically bind to EpCAM and which demonstrates superior tumor penetrating ability.

BACKGROUND OF THE INVENTION

The epithelial cell adhesion molecule EpCAM (also known as CD326 or ESA) is a pleiotropic molecule, capable of both promoting and preventing epithelial cell-cell adhesion. It is a 30-40 kDa type I glycosylated membrane protein expressed at a low level in a variety of human epithelial tissues. EpCAM is overexpressed in most solid cancers. For example, intense expression of EpCAM is found in more than 98% of patients with colorectal cancer. Two decades of studies have shed light on the roles the EpCAM plays in tumorigenesis. Rather than antagonising apoptosis, EpCAM acts by inducing proliferation with a direct impact on cell cycle control upregulating the proto-oncogene c-myc and cyclins A and E, and signal transduction into the cell nucleus by way of the Wnt pathway.

It has recently been recognised that a small proportion of cancer cells possess unlimited proliferation potential and are able to self-renewal and to generate differentiated cancer cell progeny. These so-called cancer stem cells (CSCs) are resistant to chemotherapy and radiotherapy. It is thought that cytotoxic drugs and radiation kill mainly the bulk tumor cells but spare the cancer stem cells. Thus, in order to effectively eradicate cancer, one must target and eliminate cancer stem cells as well as their progeny cells.

Epithelial cell adhesion molecule has been identified to be a cancer stem cell marker in a number of solid cancers, including breast cancer, colorectal cancer, pancreatic cancer, and liver cancer. Expression of EpCAM in various cancers appears to be inversely related to the prognosis of the patients (Baeuerle P A et al (2007). Br J Cancer 96:417-23). Initial clinical trials with anti-EpCAM antibodies failed to provide objective clinical response. It is thought that the large size of the antibody is a limitation to the distribution and delivery of monoclonal antibodies. In addition, the antibody dependent cytotoxicity relies on the carbohydrate composition in the CH2 of the antibody, which can vary significantly during antibody production. Thus, a smaller and more effective EpCAM targeting molecule is needed for targeted cancer therapy.

SUMMARY OF THE INVENTION

Given the varying success of current anti-EpCAM antibody therapy, the inventors sought to develop a nuclease-resistant RNA aptamer targeting the EpCAM cancer stem cell marker. Because aptamers are 10-20 times small than an antibody, they have superb tissue penetration properties and are, therefore, advantageous over antibodies in cancer targeting. While aptamers show great promise, there have been limited reports of their use as probes for immunohistochemistry. While not wishing to be bound by theory, it has been suggested that one of the difficulties associated with substituting aptamer for antibodies in histological protocols could be from their non-specific staining due to electrostatic attraction of these polyanion nucleic acid aptamers to positively charged sites, such as histones, present in nuclei.

The present disclosure describes an RNA aptamer against EpCAM which has diagnostic and therapeutic potential.

The present disclosure provides an isolated RNA aptamer which specifically binds to EpCAM, wherein the aptamer is not DT3 having the sequence 5'-GCGACUGGUUACCCG-GUCG-3' (SEQ ID NO:1).

The present disclosure provides an isolated RNA aptamer which specifically binds to EpCAM, the aptamer comprising the sequence 5'-ACGUAUCCCUUUUCGCGUA-3' (SEQ ID NO:2). In one example, the EpCAM is human EpCAM.

In one example, the aptamer of the present disclosure has a dissociation constant for EpCAM expressed on breast tumor cell lines of about 90 nM or less. In another example, the dissociation constant is about 65 nM or less. In another example, the dissociation constant is about 45 nM or less. In another example, the dissociation constant is about 87 nM for MDA-MB-231 cells. In another example, the dissociation constant is about 64 nM for MCF7 cells. In another example, the dissociation constant is about 41 nM for T47D cells.

In another example, the aptamer of the present disclosure has a dissociation constant for EpCAM expressed on a colon cancer cell line (HT29 cells) of about 37 nM.

In another example, the isolated RNA aptamer consists essentially of the sequence of SEQ ID NO:2.

In another example, the isolated RNA aptamer consists of the sequence of SEQ ID NO:2.

In another example, the isolated RNA aptamer comprises the sequence of SEQ ID NO:2, wherein the sequence length is between 19 and 100 bases. In another example, the sequence length is between 19 and 40 bases. In another example, the sequence length is between 19 and 30 bases. In another example, the sequence length is between 19 and 25 bases. The term "base" as used herein is understood to mean a nucleotide base or residue which is guanine (G), adenine (A), uracil (U) or cytosine (C). The bases may form hydrogen bonds between cytosine and guanine, adenine and uracil and between guanine and uracil.

In another example, the sequence comprises one or more substitutions within the sequence of SEQ ID NO:2. In another example, the sequence comprises at least one, two, three, four, five or six substitutions within the sequence of SEQ ID NO:2. In another example, the sequence comprises at least one, two, three, four, live or six substitutions within the stem region of the aptamer according to SEQ ID NO:2. In one example, the stem region is that of the predicted two dimensional structure of the aptamer.

In one example, the aptamer comprises one or more modifications (modified aptamer) that improve aptamer stability (in vitro or in vivo). Suitable modifications are discussed elsewhere herein. In one example, the pyrimidine bases are 2'-fluoro (2'-F) modified. In another example, the 3' end of the RNA aptamer is modified to protect it from nuclease digestion. In another example, aptamer is modified by coupling the 5' end to a fluorophore or inverted dT or to a PEG molecule.

The present disclosure also provides an isolated RNA aptamer having substantially the same ability to bind to EpCAM as that of an aptamer comprising a sequence of SEQ ID NO:2, wherein the aptamer is not DT3 having the sequence 5'-GCGACUGGUUACCCGGUCG-3' (SEQ ID NO:1).

In one example, the aptamer specifically binds to EpCAM+ cell(s). In another example, the EpCAM+ cell(s) is a stem cell(s). In another example, the stem cell is an isolated cancer stem cell(s). In another example, the cancer stem cell(s) is characterised as (i) expressing EpCAM, (ii) is tumorigenic, (iii) is capable of self renewal (iv) is capable of differentiating and (v) resistant to apoptosis by conventional therapy.

The cancer stem cells may be alternatively described as isolated, enriched or purified from a source, such as a biological sample. In another example, the cancer stem cell(s) represent a population of cells enriched on the basis of EpCAM+ expression. In another example, the population of cells comprises at least 30%, 40%, 50%, 60%, 70%, 80%, 90% or 95% cancer stem cells.

In one example, the EpCAM expressing cells and/or cancer stem cells are present in vivo. In another example, the EpCAM expressing cells and/or cancer stem cells are present in vitro. In a further example, the EpCAM expressing cells and/or cancer stem cells are present in a biological sample obtained from a subject.

In another example, the EpCAM expressing cells and/or cancer stem cells of the present disclosure may express one or more additional antigens including CD44, ABCG2, β-catenin, CD117, CD133, ALDH, VLA-2, CD166, CD201, IGFR, and EGF1R.

In another example, the cancer stem cell according to the present disclosure is a breast cancer stem cell, a prostate cancer stem cell, a pancreatic cancer stem cell, a colon cancer stem cell, a liver cancer stem cell, a lung cancer stem cell, an ovarian cancer stem cell, or a head and neck cancer stem cell.

The present disclosure also provides a diagnostic agent comprising an RNA aptamer as described herein.

In one example, the diagnostic agent comprises an RNA aptamer of the present disclosure coupled to a detectable label.

It would be appreciated by persons skilled in the art that the aptamers of the present invention avoid complications that may be associated with non-specific antibody binding and hence provide superior signal to noise ratio.

In one example, the diagnostic agent as described herein is used to detect for EpCAM expressing cancer stem cells in vivo or in vitro.

In one example, the RNA aptamer of the present disclosure can be used diagnostically to detect the presence of EpCAM expressing cells and/or cancer stem cells in a subject or in a biological sample obtained from a subject having a tumor or suspected of having a tumor.

Detection can be facilitated by coupling the aptamer to a detectable label. Examples of detectable labels include various enzymes, prosthetic groups, fluorescent materials, luminescent materials, bioluminescent materials, electron dense labels, labels for MRI and radioactive materials.

The present disclosure also provides an RNA aptamer as described herein or the diagnostic agent as described herein for use in histological examination of biological samples. Methods for preparing histological preparations will be familiar to persons skilled in the art.

The present disclosure also provides an anticancer agent comprising an RNA aptamer as described herein.

In one example, the anticancer agent comprises an RNA aptamer of the present disclosure coupled to a moiety. The moiety may be selected from the group consisting of a radionuclide, a chemotherapeutic agent, an si-RNA or toxin or combination thereof. In a further example, the anticancer agent comprises an RNA aptamer-survivin siRNA conjugate comprising the sequence 5'-ACGUAUC-CCUUUUCGCGUAAAAUGUAGAGAUGCGGUGGUC-CUU-3' (SEQ ID NO:3).

In one example, the anticancer agent as described herein is used to treat a cancer in a subject. In one example, the subject is one which would benefit from treatment with the RNA aptamer of the present disclosure. In another example, the subject is one which has been diagnosed as having cancer. In another example, the subject is one having a solid tumor. In a further example, the subject is one which has a cancer selected from breast cancer, prostate cancer, pancreatic cancer, colon cancer, liver cancer, lung cancer, ovarian cancer, head and neck cancer or any other cancer in which EpCAM+ cells are present.

The aptamer of the present disclosure can be coupled to a moiety and the aptamer used to direct the moiety to the site of a tumor which comprises, or is suspected of comprising an EpCAM expressing cancer stem cell(s). Examples of moieties include toxins, radionuclides or chemotherapeutic agents which can be used to kill cancer stem cells, or imaging agents which can be used to locate and size tumors comprising EpCAM expressing cells.

The anticancer agent comprising the RNA aptamer of the present disclosure can additionally include one or more effective ingredients.

The present disclosure also provides a method for isolating, purifying or enriching an EpCAM expressing cell(s) and/or cancer stem cell(s) from a biological sample obtained from a subject, the method comprising contacting the cell with an RNA aptamer of the present disclosure or the diagnostic agent of the present disclosure. In one example, the method is carried out in vitro.

Methods isolating, purifying or enriching EpCAM expressing cells are known to persons skilled in the art and are also described elsewhere herein.

The present disclosure also provides a method for identifying an EpCAM expressing cell(s) and/or cancer stem cell(s) in a subject or in a biological sample obtained from a subject having, or suspected of having cancer, the method comprising contacting the cell with an isolated RNA aptamer of the present disclosure or the diagnostic agent of the present disclosure.

The present disclosure also provides a method for treating or preventing cancer in a subject comprising providing a subject with an RNA aptamer as described herein or the anticancer agent as described herein.

In one example, the cancer is any cancer in which EpCAM expressing cells and/or cancer stem cells are present or suspected of being present. In another example, the subject is one which has been diagnosed as having cancer. In another example, the subject is one having a solid tumor. In a further example, the subject is one which has a cancer selected from brain cancer, breast cancer, prostate cancer, pancreatic cancer, colon cancer, liver cancer, lung cancer, ovarian cancer, skin cancer or any other cancer in which EpCAM$^+$ cells are present.

The present disclosure also relates to the use of an RNA aptamer or anticancer agent as described herein in medicine.

The present disclosure also relates to the use of an RNA aptamer or anticancer agent as described herein for treating or preventing cancer in a subject.

The present disclosure also relates to the use of an RNA aptamer or anticancer agent as described herein in the manufacture of a medicament for treating or preventing cancer in a subject.

The present invention also relates to a delivery agent comprising an RNA aptamer as described herein coupled to an siRNA or ribozyme. In one example, the delivery agent comprises an RNA aptamer-survivin siRNA conjugate comprising the sequence 5'-ACGUAUC-CCUUUUCGCGUAAAAUGUAGAGAUGCGGUGGUC-CUU-3' (SEQ ID NO:3)

The present disclosure also provides a composition comprising a therapeutically effective amount of an RNA aptamer, anticancer agent or delivery agent as described herein, together with a pharmaceutically acceptable carrier and/or excipient.

The present disclosure also provides an RNA aptamer as described herein or the diagnostic agent as described herein for use in molecular imaging of tumors.

The tumor penetrative ability of the RNA aptamer of the present invention provides a distinct advantage over antibodies for molecular imaging of tumors. For example, the RNA aptamer can be coupled to an agent which facilitates the detecting and imaging of tumors bearing EpCAM expressing cells. Examples of suitable agents include the detection labels are described herein.

The RNA aptamer, diagnostic agent, anticancer agent, delivery agent or pharmaceutical composition as described herein may be used alone or in combination with other treatment modalities. For example, the RNA aptamer, diagnostic agent, anticancer agent, delivery agent or pharmaceutical composition may be used in combination with chemotherapy and/or radiotherapy. While not wishing to be bound by theory, it is postulated that the chemotherapy or radiotherapeutic agents can be use to shrink tumors by primarily targeting rapidly dividing cells which are typically the progeny cells of the cancer stem cells. The diagnostic agent can be used to determine the effectiveness of any prior treatment modality to eliminate cancer stem cells by detecting the presence or absence of cancer stem cells in the tumor. The anticancer agent, delivery agent or pharmaceutical composition containing the RNA aptamer of the present disclosure can then be administered to the site of the tumor to specifically deplete cancer stem cells. Accordingly, the anticancer agent, delivery agent or pharmaceutical composition containing the RNA aptamer can be used together with chemotherapy or radiotherapy or subsequent to chemotherapy or radiotherapy treatment. It is also contemplated that the RNA aptamer of the present disclosure can be combined with one or more additional aptamers which target an antigen present on a cancer stem cell.

Each example of the disclosure shall be taken to apply mutatis mutandis to a method for treating, preventing or ameliorating cancer in a subject.

Each example of the disclosure shall be taken to apply mutatis mutandis to molecular imaging of tumors.

A: Immunofluorescence staining of breast cancer (T47D, MCF7 and MDA-MB-231), colon cancer (HT-29) and glioblastoma (U118MG) xenograft tumours by EpCAM aptamers, DT3 and 23, control aptamer and the anti-EpCAM antibody, 323/A3 (Blue: nuclei; Red: EpCAM positive staining). B: Immunohistochemistry was performed with the anti-EpCAM antibody BerEP4, and all tumours were evaluated by haematoxylin and eosin staining for morphological confirmation. Aptamer staining was performed for 15 min at 37° C., while 323/A3 staining was performed at 4° C. overnight and BerEP4 was performed at room temperature for 20 min. All fluorescent images were taken at 60×, while light microscopy images were taken at 20×. Images are representative of at least three separate experiments. Scale bar: 50 μm.

Figure 2:
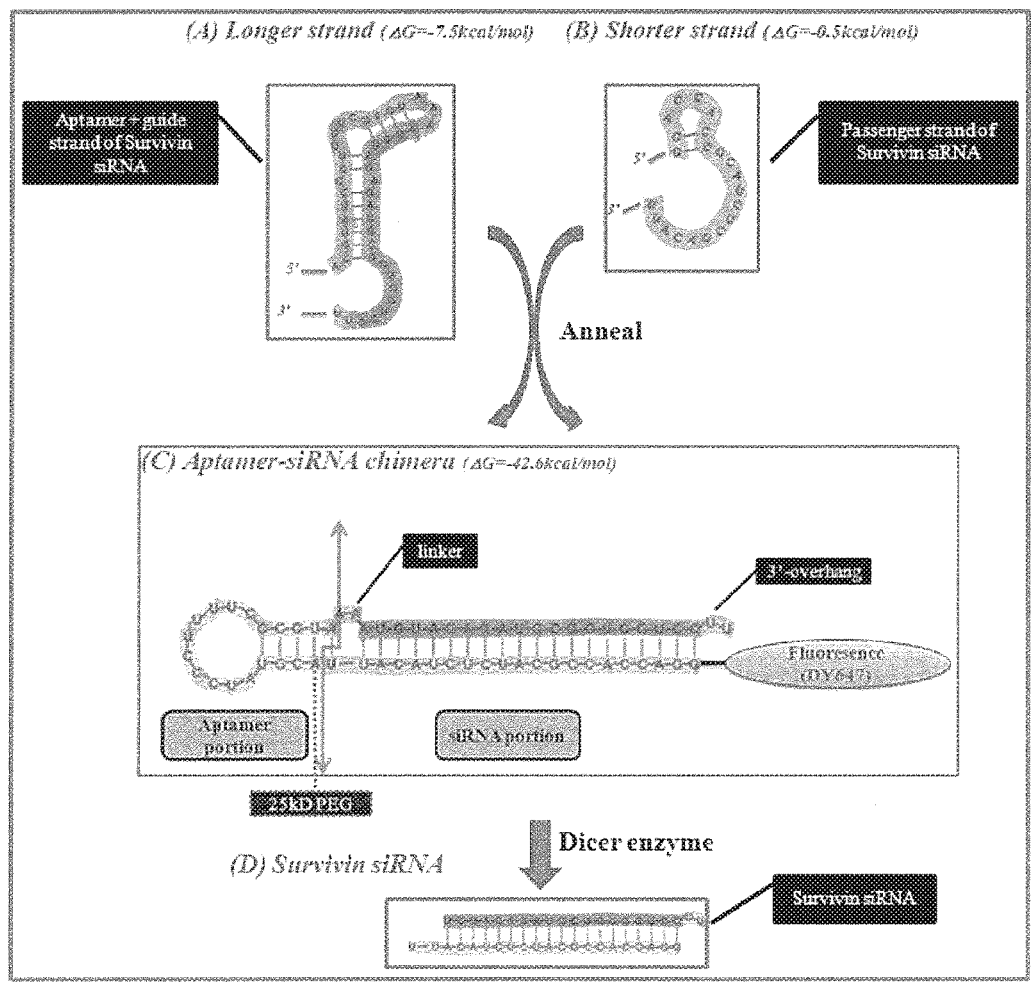

FIG. 2. Structure of the EpCAM aptamer-siRNA chimera

The chimera for in vivo delivery of siRNA directed by EpCMA aptamer is consisted of three elements, the guided strand of siRNA linked to the EpCMA aptamer (A), the passenger strand of siRNA (B) and a liker. FIG. 2C shows the assembled siRNA-aptamer chimera. To facilitate molecular imaging, a Dy647 fluorescence dye is attached to the 5'-end of the passenger strand of siRNA (C). The predicted final produce after processing by Dicer enzyme in the cytoplasm is shown in (D).

Figure 3:
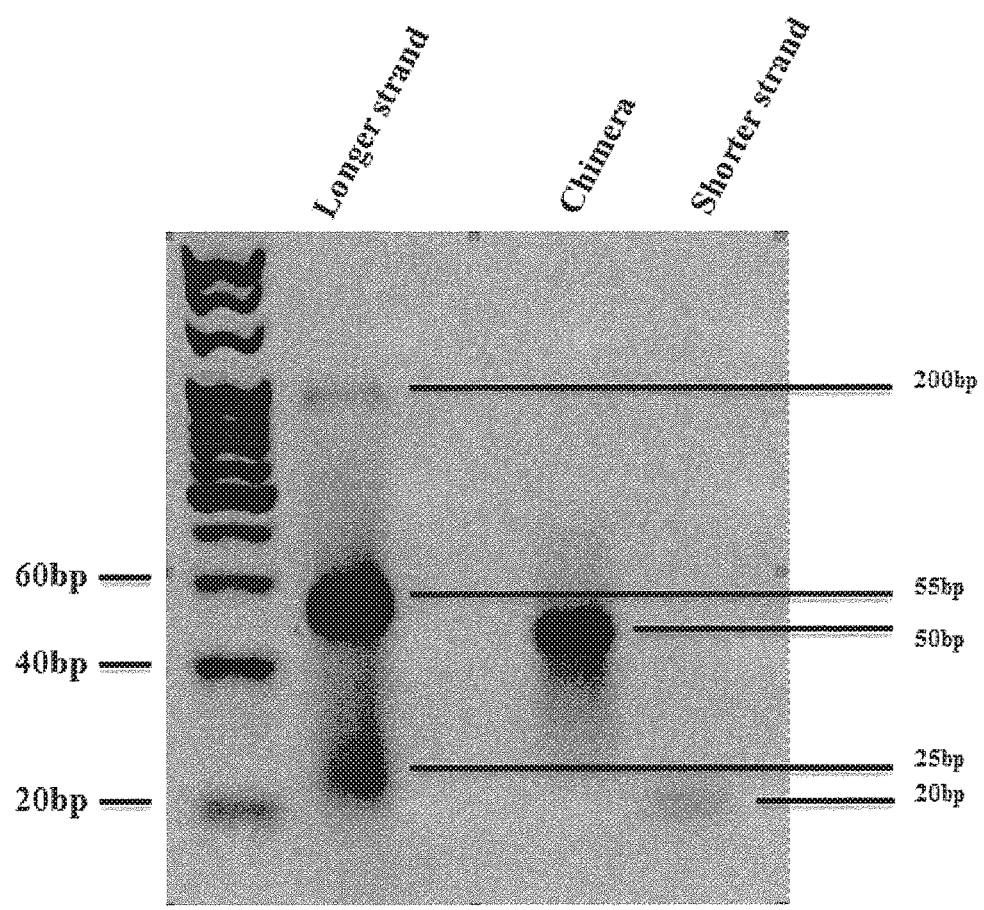

FIG. 3. Analysis of chimera with native agarose gel.

After annealing, the length of the chimera and individual components were analysed in a 2% non-denaturing agarose gel. The RNA was stained with GelStar©. Analysis of the longer strand resulted in three bands (25 bp, 55 bp and 200 bp respectively), which is possibly related to its unstable, complex structure (ΔG −7.5 kcal/mol for 43nt), while only one band was detected for the shorter strand (20 bp, ΔG −0.5 kcal/mol for 21nt). Following annealing of both strands, a single band was visualised (Chimera 50 bp), suggesting a new stable structure was created (ΔG −42.6 kcal/mol for 64nt).

Figure 4:
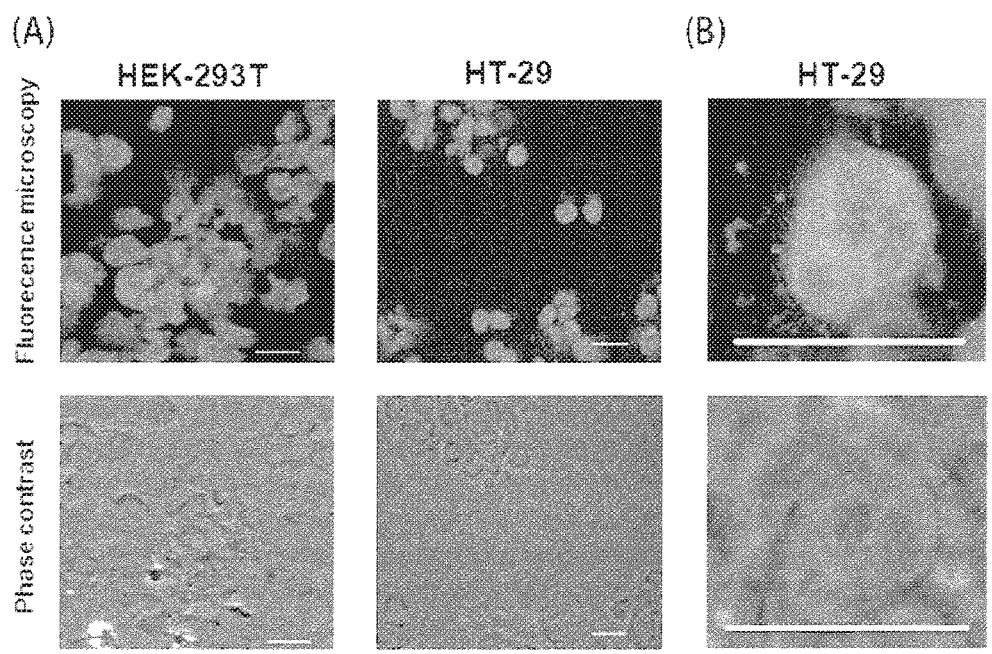

FIG. 4. EpCAM aptamer-siRNA chimera is internalised specifically by EpCAM positive HT-29 colonic adenocarcinoma cells.

DY-647-labelled EpCAM aptamer-siRNA chimera was incubated with indicated human cancer cells for 30 min at 37° C., followed by visualisation using laser scanning confocal microscopy. For each pair of panels, fluorescent images are across the top and optical (phase contrast) images are below. (A) Binding and subcellular distribution of chimeras to HEK-293T (EpCAM negative) and HT-29 (EpCAM positive) cancer cell lines. (B) Enlarged micrograph showing punctuate pattern of fluorescently-labelled EpCAM aptamer-siRNA chimera in single HT-29 cell. Scale bar=20 μm.

Figure 5:
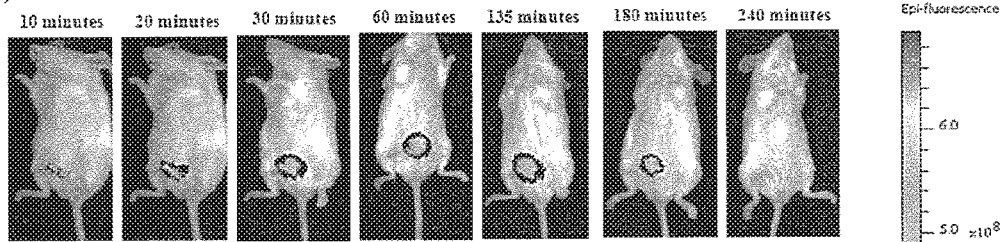
Figure 5:
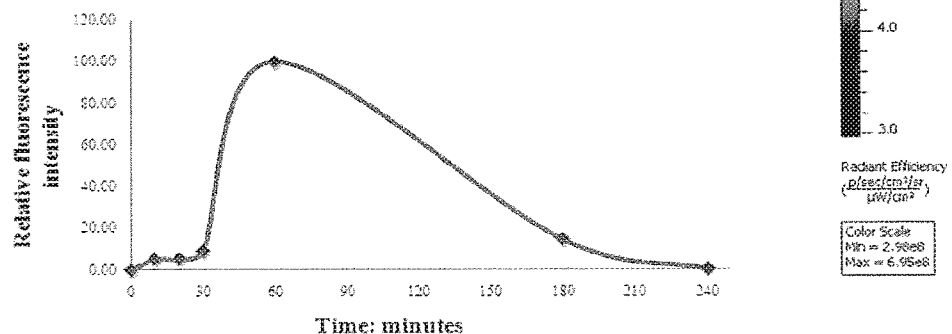
Figure 5:
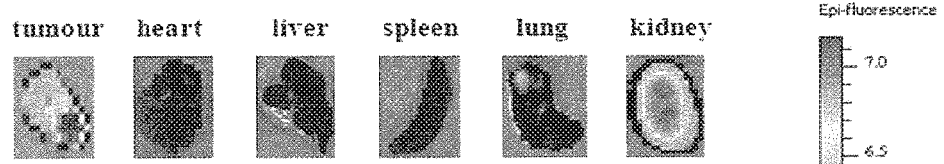
Figure 5:
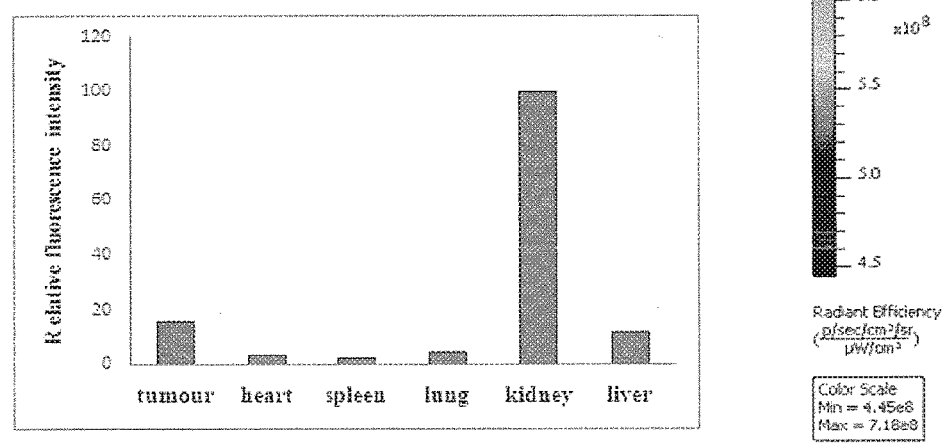

FIG. 5. In vivo targeting efficacy of aptamer-siRNA chimera in a xenograft model of breast tumor.

(A) T47D ductal carcinoma cells (EpCAM positive) were orthotopically xenotransplanted into the 4th mammary gland of 8-week old NOD/SCID mice. When tumors reached a volume of approx 0.2 cm$^3$, the Dy647-labelled siRNA-EpCAM aptamer chimera was administered with chimera (1 nmol/mouse) through tail vein injection. After injection, fluorescence density was measured using a Xenogen IVIS Lumina II imaging system at different time points as shown. (B) Relative fluorescence signal intensity-time profiles of chimera. The fluorescence values of each time point was normalised with background (fluorescence value measured at 0 minute). (C) Four hours after injection, when fluorescence disappeared from live animal imaging, tumor and organs shown in the figure were dissected and the fluorescence intensities were measured immediately using a Xenogen IVIS Lumina II imaging system. (D) The biodistribution and tumor uptake profile for siRNA-aptamer chimera. The fluorescence values from each organ and the tumour were normalised with fluorescence value of the background. The relative chimera amounts are shown in the histogram on the right.

Figure 6:
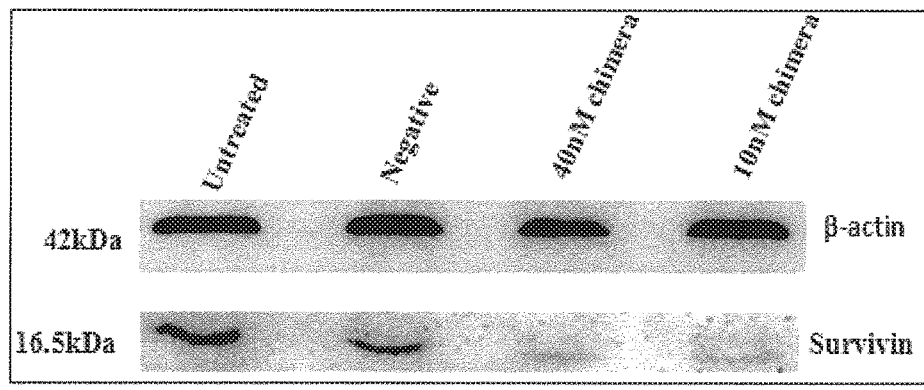
Figure 6:
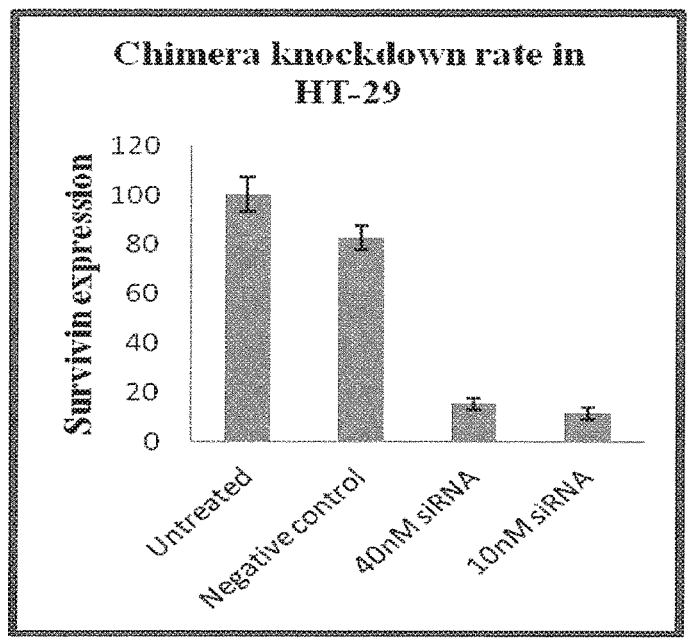

FIG. 6. EpCAM aptamer-siRNA chimera mediated inhibition of survivin expression.

Without using transfection agent, such as Lipofectamine 2000, the HT-29 cells were incubated with different concentrations of chimera (10 nM and 40 nM) in the full cell culture medium (containing 10% feral calf serum) for 24 hr. After washing with PBS three times, the cells were incubated with the growth medium for a further 48 h followed by cell lysis, separation on a 12% SDS-PAGE gel and Western analysis (A) Western blot analysis of survivin protein in HT-29 cells. β-actin was served as an internal loading control. (B) The knock down of survivin protein by siRNA-aptamer chimera. The surviving expression levels were normalised as the ratio of survivin protein expression levels to that of β-actin protein.

Figure 7:
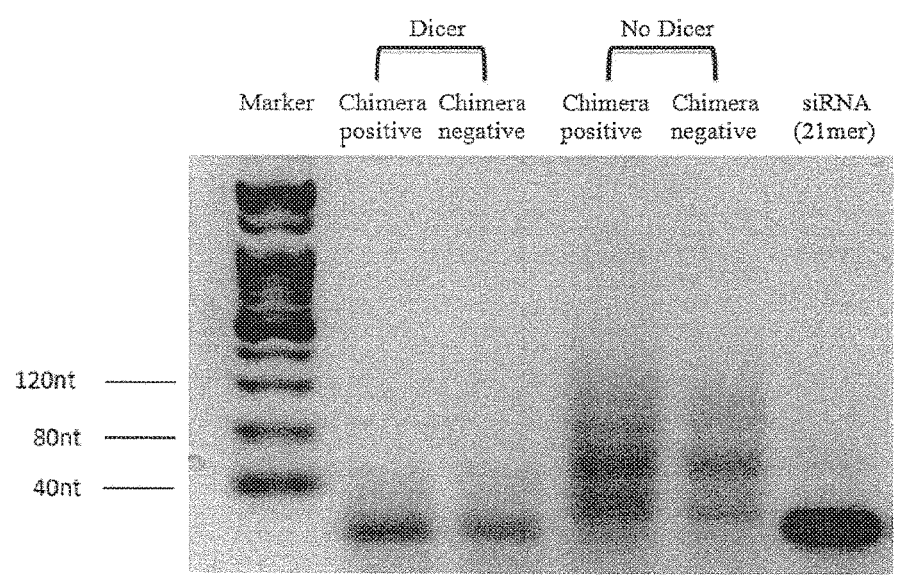

FIG. 7. In vitro Dicer processing of chimera.

Chimeras were incubated with recombinant human Dicer enzyme (1 unit/reaction) for 12 hours. The products of Dicer cleavage or uncleavaged products were visualized on 4% Metapher agrose gel. The negative control chimera is the chimera without the passenger strand. A double-stranded surviving siRNA was used as a control to mark the position of a 21-mer double-stranded RNA on the gel.

Figure 8:
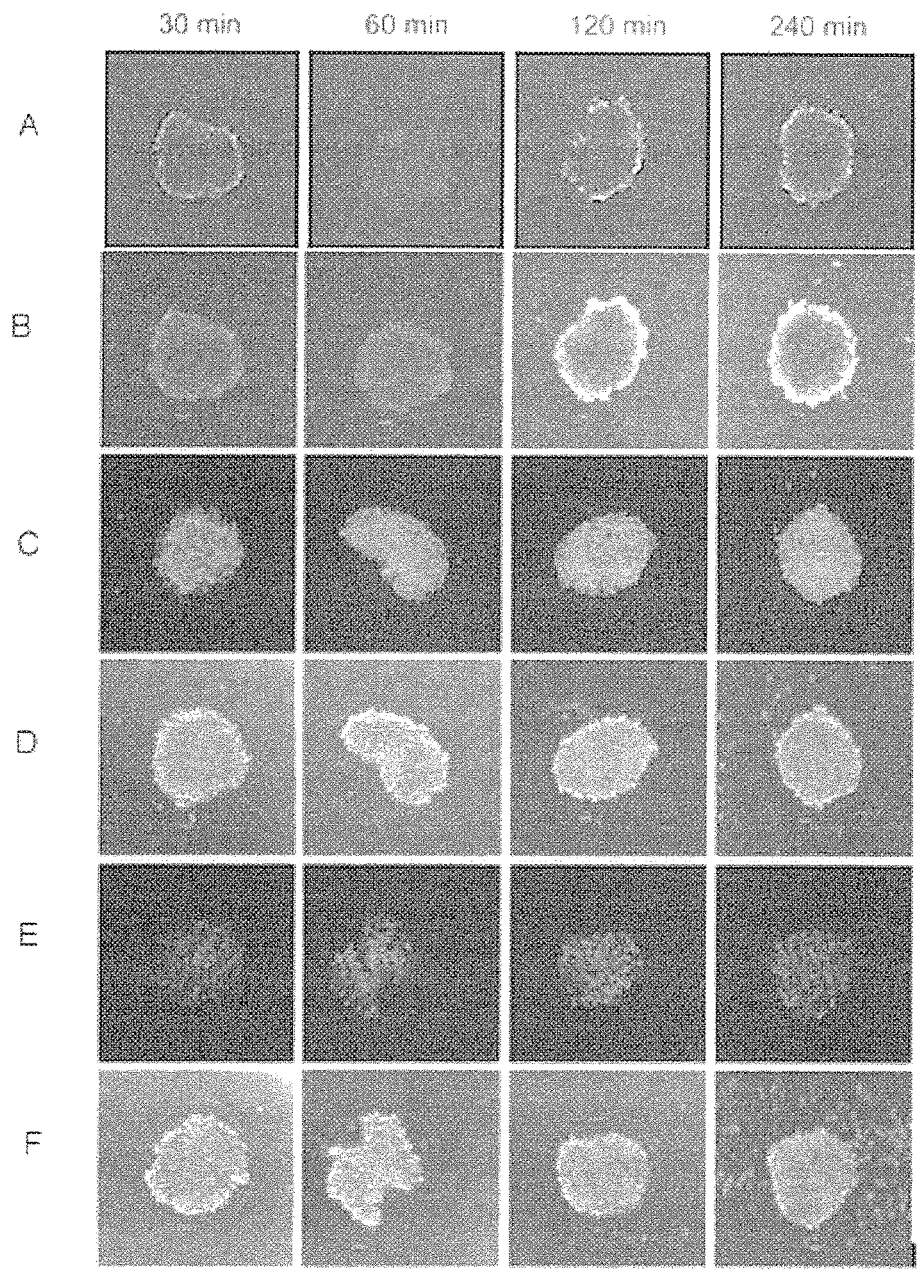

FIG. 8. Effective penetration of aptamer 23 into tumor sphere in vitro.

HT-29 or HEK293T cells were cultured in stem cell culture medium (DMEM/F12 with 20 ng/ml EGF and FGF and B27). When tumour sphere reached a size of ~300-400 µm, the sphere were incubated with 100 nM PE-labelled anti-EpCAM antibody, DY647-labelled EpCAM aptamer-23 or a DY647-labelled control aptamer that does not bind to EpCAM. After incubating for 0.5, 1, 2 or 4 h, the spheres were washed twice with PBS and imaged via fluorescence confocal microscopy. A phase contrast image of the sphere was also taken for each sample. Panel A fluorescence image for antibody EpCAM, Panel B phase contrast image for tumor sphere. Panel C: fluorescence image for aptamer EpCAM 23, Panel D: phase contrast image for tumor sphere. Panel E: fluorescence image aptamer control, Panel F: phase contrast image for tumor sphere.

Figure 9:
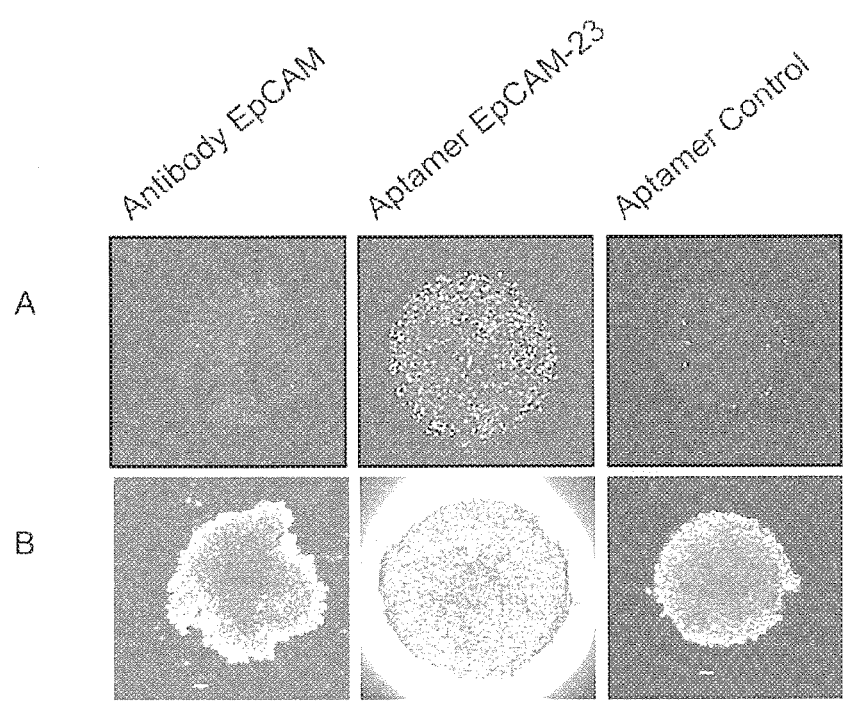

FIG. 9. Aptamer retention in tumor sphere.

Tumour spheres were incubated with EpCAM antibody, aptamer-23 or control aptamer for 4 h. After washing with PBS twice, the tumor spheres were incubated with the culture medium for a further 24 h followed by confocal microscopy. Panel A: fluorescence image for antibody or aptamer. Panel B: phase contrast image for tumour sphere.

Figure 10:
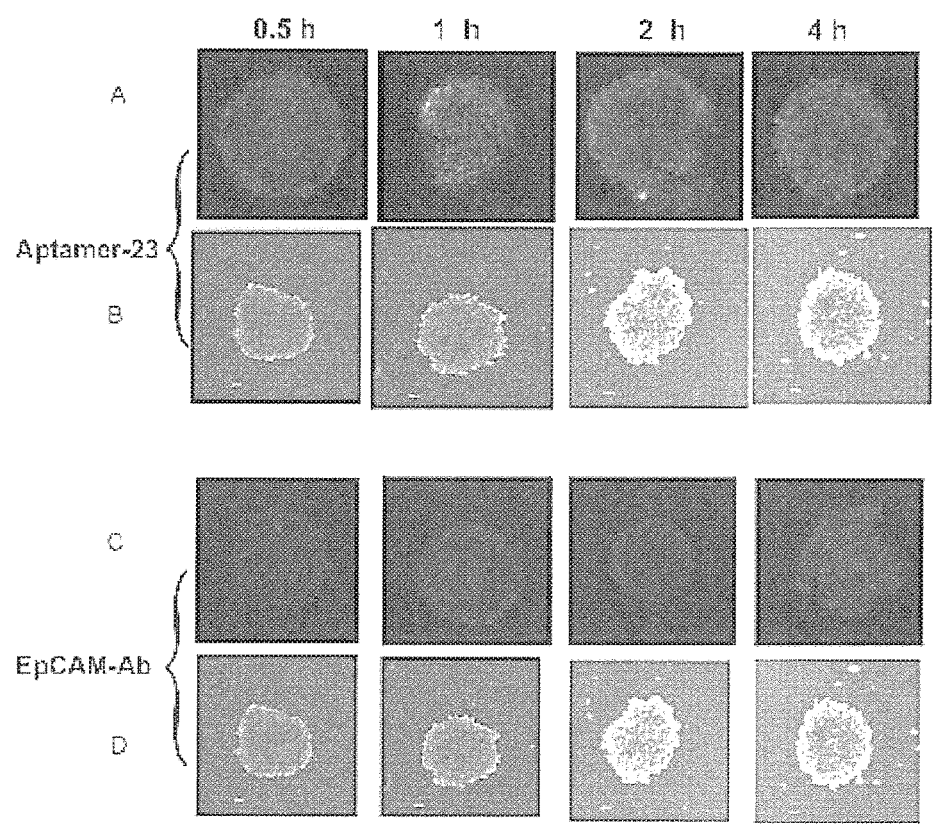

FIG. 10. The specificity and selectivity of aptamer-23 in the penetration of tumor sphere.

After four hour incubation with EpCAM antibody or aptamer 23 separately, the tumor spheres were washed twice with PBS and were cultured for a further 24 h followed by confocal microscopy. Panel A: fluorescence image for aptamer 23. Panel B: phase contrast for tumor sphere. Panel C: fluorescence image for anti-EpCAM antibody. Panel D: phase contrast image for tumour sphere.

Figure 11:
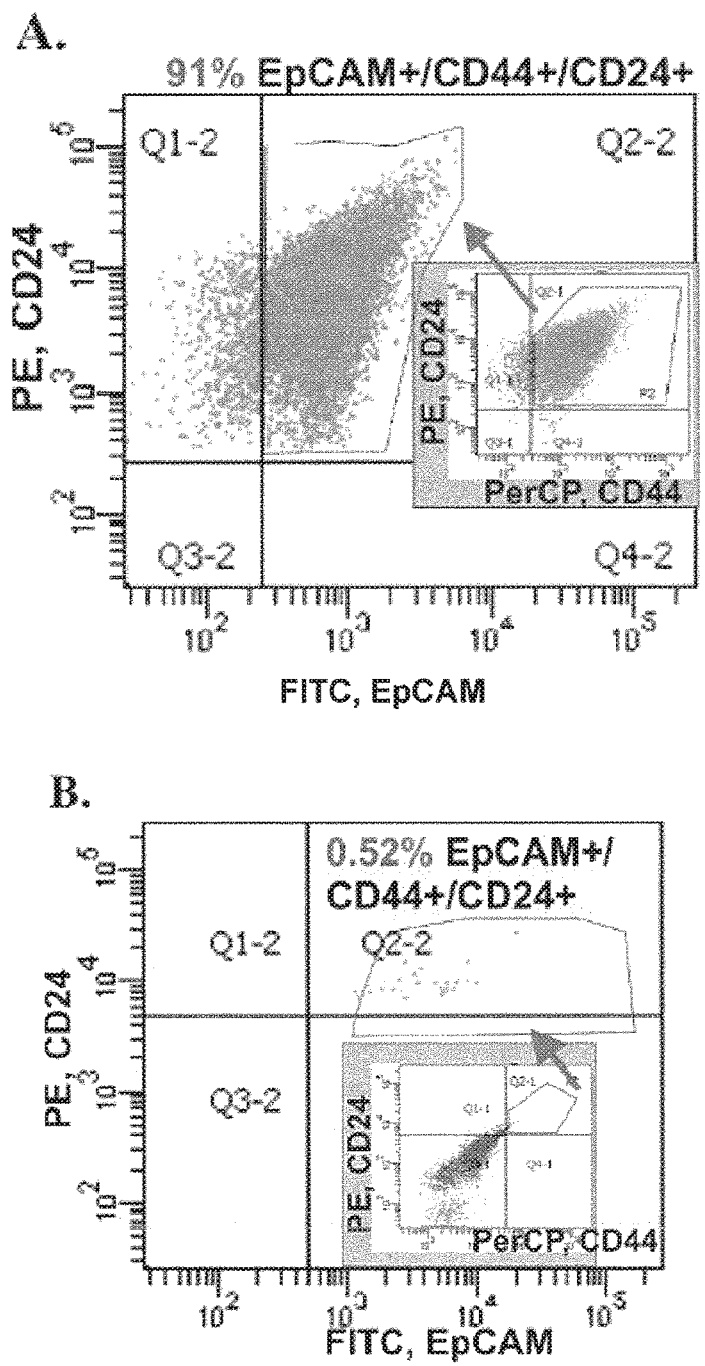

FIG. 11. CSC marker analysis after treatment

Flow cytometry analysis of EpCAM, CD44 and CD24 expression in HT29 spheres treated with EpCAM aptamer-Dox (B) or Dox alone (A).

Figure 12:
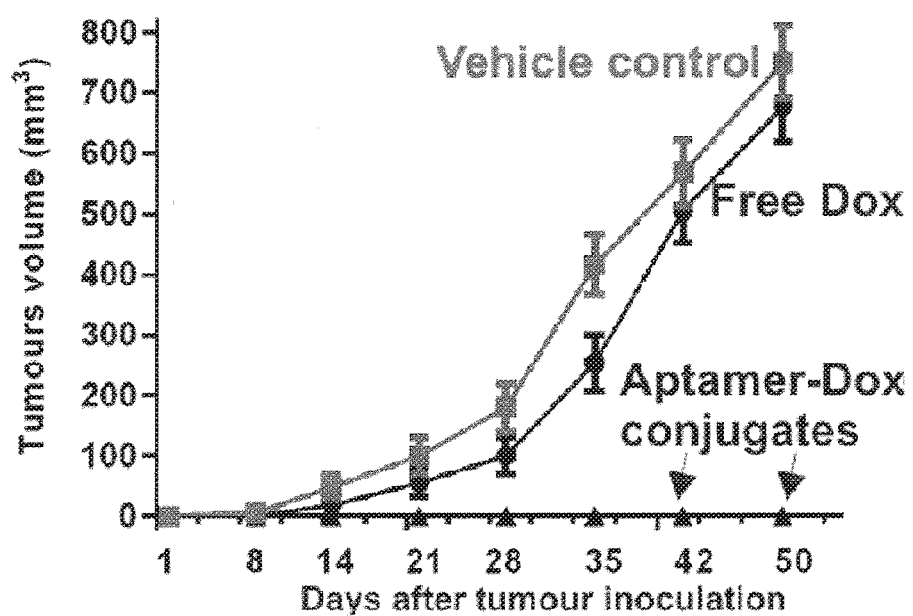

FIG. 12. Effect of in vitro treatment on tumour growth in vivo.

HT29 xenograft tumour size (in volume) was measured against time in mice administered Dox-treated cells or EpCAM aptamer-Dox treated cells.

Figure 13:
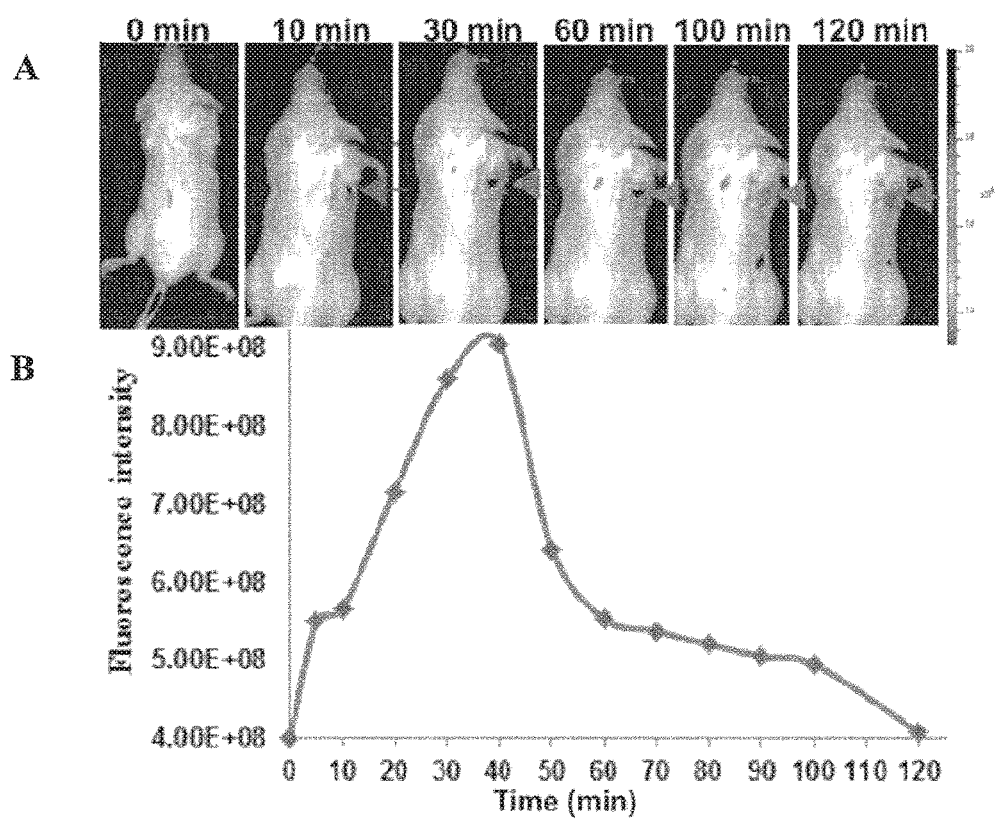

FIG. 13. Live animal imaging

Time course of HT29 tumour fluorescence following a single i.v. injection of 0.75 nmole Dy647-aptamer-Dox.

Figure 14:
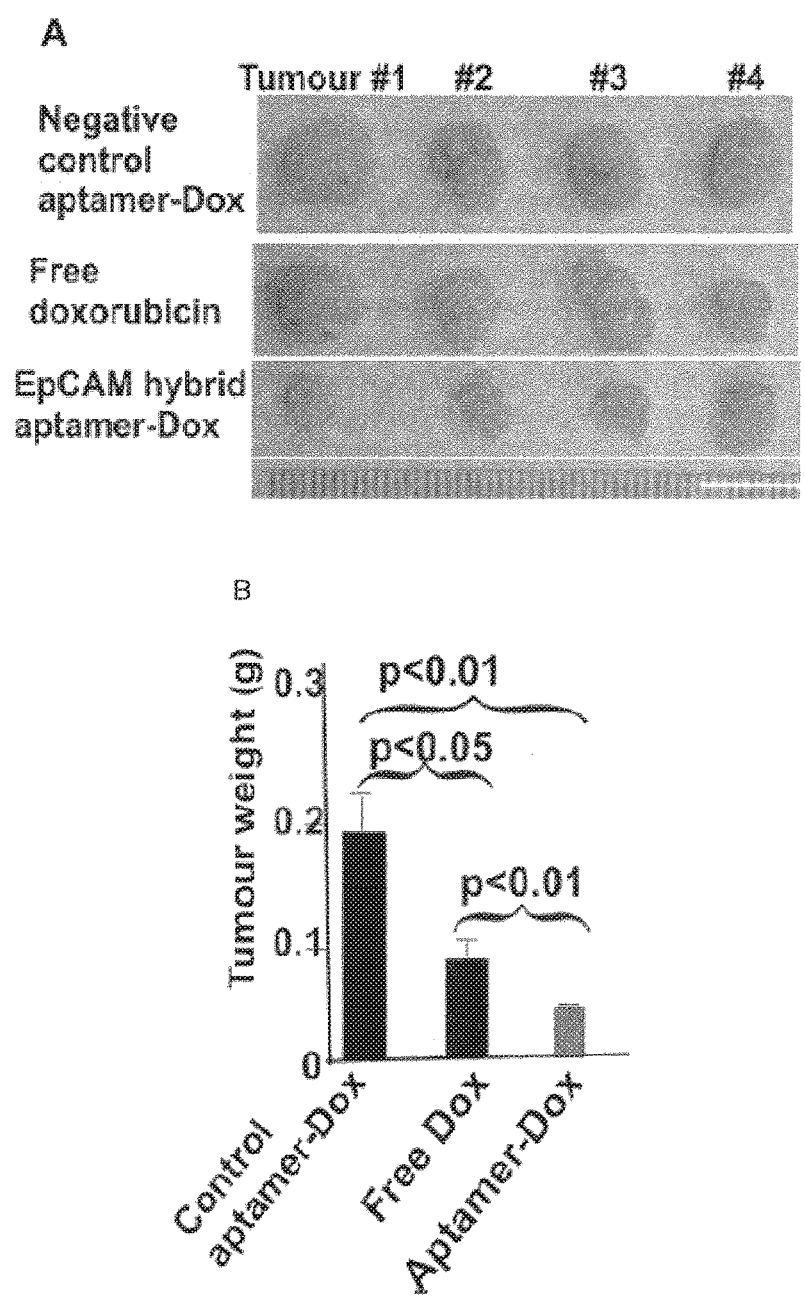

FIG. 14. In vivo treatment efficacy of aptamer-Dox

Tumours excised from mice bearing HT29 xenograft tumours treated with Doxorubicin only or EpCAM aptamer-Dox (A). Mean tumour weights (B).

Figure 15:
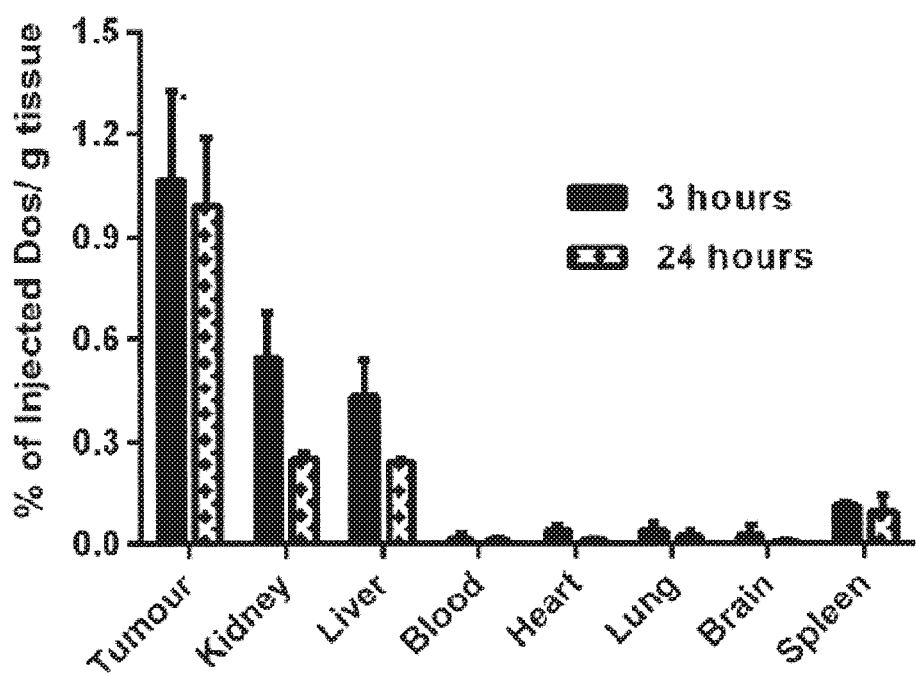

FIG. 15. Biodistribution and in vivo stability of PEG-aptamer-Dox

PEG-aptamer-Dox (5 mg Dox/kg) was injected i.v. into NOD/SCID mice bearing HT-29 colon cancer xenograft (s.c). The percentage (%) injected dose (ID) of PEG-aptamer normalised by the weight of a given tissue/organ (in g) as determined via aptamer ELISA is plotted in the bar chart.

Figure 16:
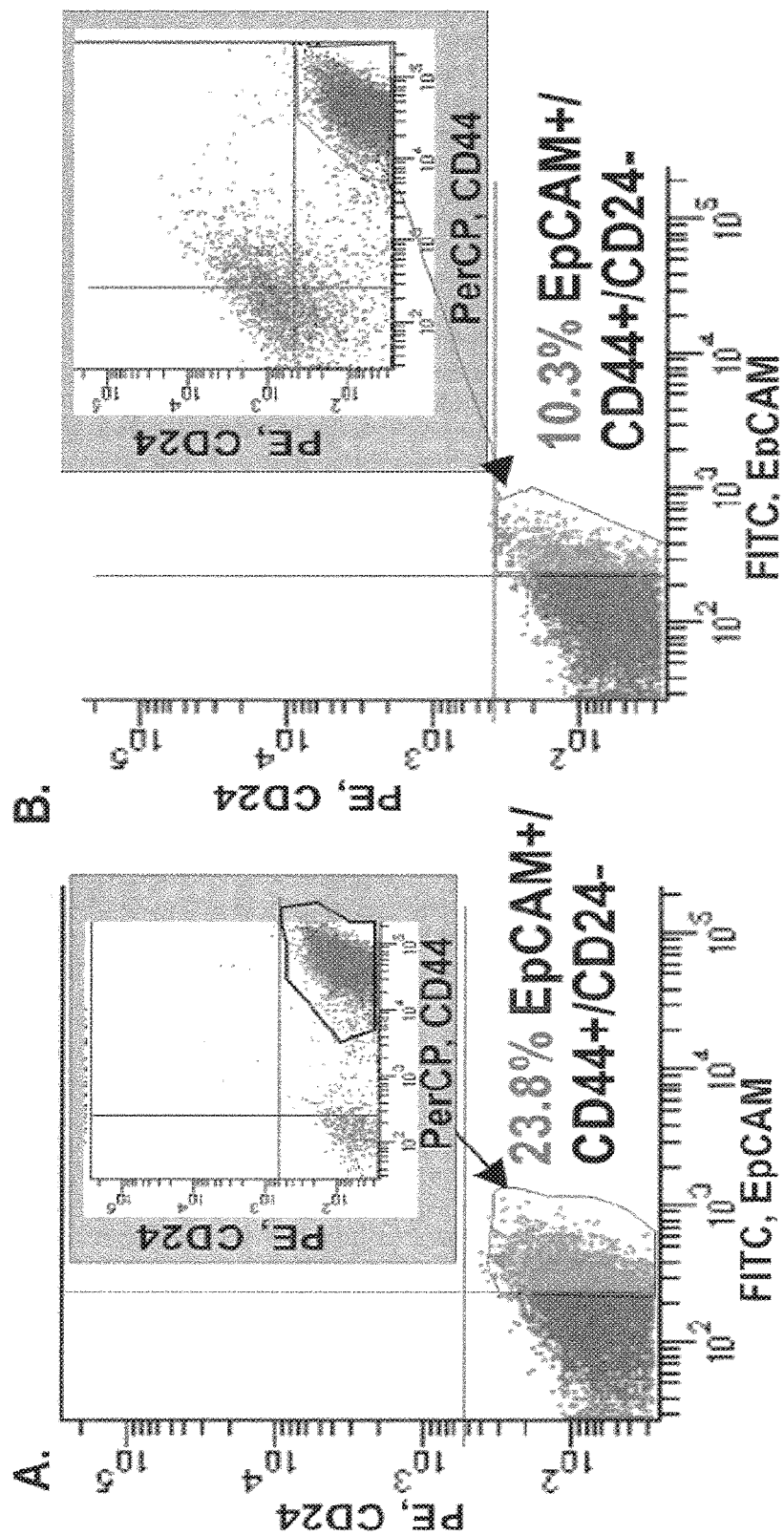

FIG. 16. Examples of CSC marker analysis

Expression by flow cytometery of EpCAM, CD44 and CD24 in MCF-7/ADR tumourspheres treated (i.v.) with EpCAM aptamer-siRNA chimera and Dox (B) versus treatment with Dox alone (A).

Figure 17:
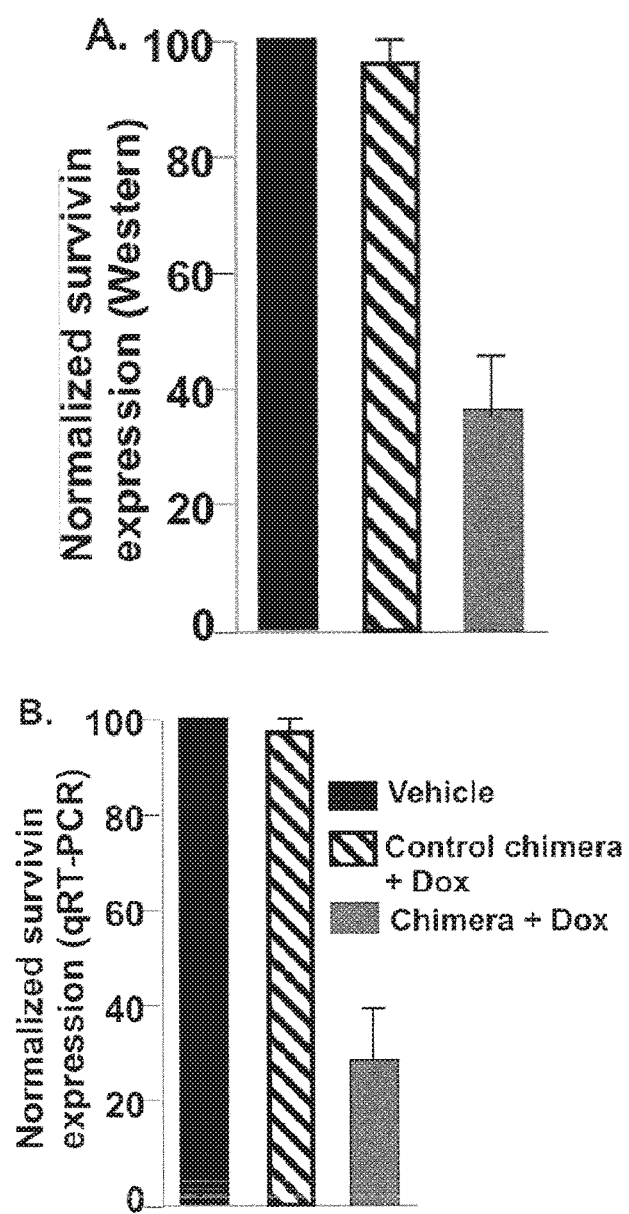

FIG. 17. In vivo efficacy of knocking down of survivin by aptamer-siRNA chimera in MCF-7/ADR tumour xenograft model (n=5)

Survivin expression by Western (A) or by quantitative RT-PCT (B) demonstrating in vivo efficacy of the in vivo tumour-targeted RNAi by EpCAM aptamer-siRNA chimera.

Figure 18:
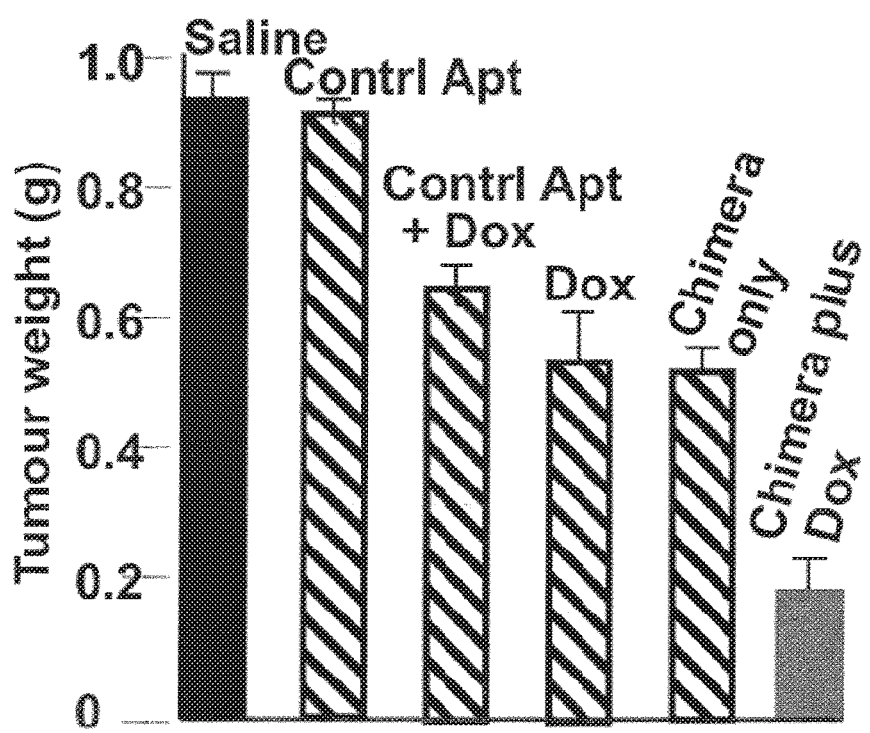

FIG. 18. Tumour weight after 3 treatments (n=8)

MCF-7/ADR tumour bearing mice were treated on days 1, 3 and 5 with an i.v. bolus injection of EpCAM aptamer-siRNA PEG chimera and day 2, 4, 6 with an i.v. bolus of doxorubicin. Two days alter the last (third) treatment, tumours were removed and weighed.

KEY TO SEQUENCE LISTING

SEQ ID NO: 1 is a nucleotide sequence of an aptamer which specifically binds to EpCAM;

SEQ ID NO: 2 is a nucleotide sequence of an aptamer which specifically binds to EpCAM;

SEQ ID NO: 3 is a nucleotide sequence of an aptamer-siRNA chimera which specifically binds to EpCAM;

SEQ ID NO:4 is a nucleotide sequence of a DNA sense oligonucleotide;

SEQ ID NO:5 is a nucleotide sequence of a DNA antisense oligonucleotide;

SEQ ID NO:6 is a nucleotide sequence of a DNA sense oligonucleotide;

SEQ ID NO:7 is a nucleotide sequence of a DNA antisense oligonucleotide:

SEQ ID NO:8 is nucleotide sequence of a DNA sense oligonucleotide;

SEQ ID NO:9 is a nucleotide sequence of a DNA antisense oligonucleotide;

SEQ ID NO:10 is a nucleotide sequence of a DNA sense oligonucleotide;

SEQ ID NO:11 is a nucleotide sequence of a DNA antisense oligonucleotide;

SEQ ID NO:12 is a nucleotide sequence of an aptamer which binds to EpCAM;

SEQ ID NO:13 is a nucleotide sequence of a negative control aptamer.

DETAILED DESCRIPTION OF THE INVENTION

General Techniques and Selected Definitions

The term "and/or", e.g., "X and/or Y" shall be understood to mean either "X and Y" or "X or Y" and shall be taken to provide explicit support for both meanings or for either meaning.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Each example described herein is to be applied mutatis mutandis to each and every other example of the disclosure unless specifically stated otherwise.

Those skilled in the art will appreciate that the disclosure is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific examples described herein, which are intended for the purpose of exemplification only. Functionally-equivalent products, compositions and methods are clearly within the scope of the disclosure.

The present disclosure is performed without undue experimentation using, unless otherwise indicated, conventional techniques of molecular biology, recombinant DNA technology, cell biology and immunology. Such procedures are described, for example, in Sambrook, Fritsch & Maniatis, Molecular Cloning: A Laboratory Manual, Cold Spring Harbor Laboratories, New York, Second Edition (1989), whole of Vols I, II, and III; DNA Cloning: A Practical Approach, Vols. I and II (D. N. Glover, ed., 1985), IRL Press, Oxford, whole of text; Oligonucleotide Synthesis: A Practical Approach (M. J. Gait, ed, 1984) IRL Press, Oxford, whole of text, and particularly the papers therein by Gait, ppl-22; Atkinson et al, pp 35-81; Sproat et al, pp 83-115; and Wu et al, pp 135-151; 4. Nucleic Acid Hybridization: A Practical Approach (B. D. Hames & S. J. Higgins, eds., 1985) IRL Press, Oxford, whole of text; Immobilized Cells and Enzymes: A Practical Approach (1986) IRL Press, Oxford, whole of text; Perbal, B., A Practical Guide to Molecular Cloning (1984); Methods In Enzymology (S. Colowick and N. Kaplan, eds., Academic Press, Inc.), whole of series, Sakakibara, D., Teichman, J., Lien, E. Land Fenichel, R. L (1976). Biochem. Biophys. Res. Commun. 73 336-342; Merrifield, R. B. (1963). J. Am. Chem. Soc. 85, 2149-2154; Barany, G. and Merrifield, R. B. (1979) in The Peptides (Gross, E. and Meienhofer, J. eds.), vol. 2, pp. 1-284, Academic Press, New York. 12. Winsch, E., ed. (1974) Synthese von Peptiden in Houben-Weyls Metoden der Organischen Chemie (Müler, E., ed.), vol. 15, 4th edn., Parts 1 and 2, Thieme, Stuttgart; Bodanszky, M. (1984) Principles of Peptide Synthesis, Springer-Verlag, Heidelberg; Bodanszky, M. & Bodanszky, A. (1984) The Practice of Peptide Synthesis, Springer-Verlag, Heidelberg; Bodanszky, M. (1985) Int. J. Peptide Protein Res. 25, 449-474; Handbook of Experimental Immunology, Vols. I-IV (D. M. Weir and C. C. Blackwell, eds., 1986, Blackwell Scientific Publications); and Animal Cell Culture: Practical Approach, Third Edition (John R. W. Masters, ed., 2000), ISBN 0199637970, whole of text.

Throughout this specification, unless the context requires otherwise, the word "comprise", or variations such as "comprises" or "comprising", will be understood to imply the inclusion of a stated step or element or integer or group of steps or elements or integers but not the exclusion of any other step or element or integer or group of elements or integers.

The term "consists of" or "consisting of" shall be understood to mean that a method, process or composition of matter has the recited steps and/or components and no additional steps or components.

The term "about", as used herein when referring to a measurable value such as an amount of weight, time, dose, etc. is meant to encompass variations of ±20% or ±10%, more preferably ±5%, even more preferably ±1%, and still more preferably ±0.1% from the specified amount, as such variations are appropriate to perform the disclosed method.

The term "aptamer" as used herein refer in general to either an oligonucleotide of a single defined sequence or a mixture of said oligonucleotides, wherein the mixture retains the properties of binding specifically to EpCAM. As used herein, "aptamer" refers to single stranded nucleic acid. Structurally, the aptamers of the present disclosure are specifically binding oligonucleotides.

The term "oligonucleotide" as used herein is generic to polydeoxyribonucleotides (containing 2'-deoxy-D-ribose or modified forms thereof), i.e. DNA, to polyribonucleotides (containing D ribose or modified forms thereof), i.e. RNA, and to any other type of polynucleotide which is an N-glycoside or C-glycoside of a purine or pyrimidine base, or modified purine or pyrimidine base or abasic nucleotides. According to the present disclosure the term "oligonucleotide" includes not only those with conventional bases, sugar residues and internucleotide linkages, but also those that contain modifications of any or all of these three moieties.

The term "RNA aptamer" as used herein is an aptamer comprising ribonucleoside units. RNA aptamer is also meant to encompass RNA analogs as defined herein.

As used herein the term "binding affinity" and "binding activity" are intended to refer to the tendency of a ligand molecule/aptamer to bind or not bind a target and describes the measure of the strength of the binding or affinity of the ligand molecule/aptamer to bind the target. The energetics of said interactions are significant in "binding activity" and "binding affinity" because they define the necessary concentrations of interacting partners, the rates at which these partners are capable of associating, and the relative concentrations of bound and free molecules in a solution. The energetics are characterized herein through, among other ways, the determination of a dissociation constant, $K_d$. As is known in the art, a low dissociation constant indicates stronger binding and affinity of the molecules to each other. In one example, the dissociation constant is at least $10^{-6}$ M. In another example, the dissociation constant is at least $10^{-8}$ and $10^{-1}$ M.

As used herein, the term "biological sample" refers to a cell or population of cells or a quantity of tissue or fluid from a subject. Most often, the sample has been removed from a subject, but the term "biological sample" can also refer to cells or tissue analyzed in vivo, i.e. without removal from the subject. Often, a "biological sample" will contain cells from the subject, but the term can also refer to non-cellular biological material, such as non-cellular fractions of blood, saliva, or urine, that can be used to measure gene expression levels. Biological samples include, but are not limited to, tissue biopsies, needle biopsies, scrapes (e.g. buccal scrapes), whole blood, plasma, serum, lymph, bone marrow, urine, saliva, sputum, cell culture, pleural fluid, pericardial fluid, ascitic fluid or cerebrospinal fluid. Biological samples also include tissue biopsies and cell cultures. A biological sample or tissue sample can refer to a sample of tissue or fluid isolated from an individual, including but not limited to, for example, blood, plasma, serum, tumor biopsy, urine, stool, sputum, spinal fluid, pleural fluid, nipple aspirates, lymph fluid, the external sections of the skin, respiratory, intestinal, and genitourinary tracts, tears, saliva, milk, cells (including but not limited to blood cells), tumors, organs, and also samples of in vitro cell culture constituent. In some embodiments, the sample is from a resection, bronchoscopic biopsy, or core needle biopsy of a primary or metastatic tumor, or a cellblock from pleural fluid. In addition, fine needle aspirate samples can be used. Samples may be paraffin-embedded or frozen tissue. The sample can be obtained by removing a sample of cells from a subject, but can also be accomplished by using previously isolated cells (e.g. isolated by another person), or by performing the methods of the invention in vivo.

The term "coupled to" as used herein is intended to encompass any construction whereby the RNA aptamer is linked, attached or joined to a detection agent, moiety, siRNA or ribozyme as described herein. Methods for effecting coupling will be known to persons skilled in the art and include, but are not limited to conjugation, linking via peptide linker or by direct chemical synthesis of the RNA and agent (e.g. siRNA or ribozyme) as a whole chain.

The term "isolated" as used herein is intended to refer to the RNA aptamer or the stem cell (e.g. cancer stem cell), isolatable or purified from other components. An isolated cell refers to a cell from the environment in which it may naturally occur. The isolated cell may be purified to any degree relative to its naturally-obtainable state.

The term "ligand" as used herein refers to a molecule or other chemical entity having a capacity for binding to a target. A ligand can comprise a peptide, an oligomer, a nucleic acid (e.g. an aptamer), a small molecule (e.g. a chemical compound), an antibody or fragment thereof, nucleic acid-protein fusion and/or any other affinity agent. Thus, a ligand can come from any source, including libraries, particularly combinatorial libraries, such as the aptamer libraries disclosed herein below, phage display libraries, or any other library as would be apparent to one of ordinary skill in the art after review of the disclosure herein.

The term "modified RNA aptamer" as used herein is meant to refer to a polymeric molecule, which in addition to containing ribonucleosides as its units, also contains at least one of the following: 2'-deoxy, 2'-halo (including 2'-fluoro), 2'-amino (preferably not substituted or mono- or disubstituted), 2'-mono-, di- or tri-halomethyl, 2'-O-alkyl, 2'-O-halo-substituted alkyl, 2'-alkyl, azido, phosphorothioate, sulfhydryl, methylphosphonate, fluorescein, rhodamine, pyrene, biotin, xanthine, hypoxanthine, 2,6-diamino purine, 2-hydroxy-6-mercaptopurine and pyrimidine bases substituted at the 6-position with sulfur or 5 position with halo or $C_{15}$ alkyl groups, abasic linkers, 3'-deoxy-adenosine as well as other available "chain terminator" or "non-extendible" analogs (at the 3'-end of the RNA), or labels such as $^{32}P$, $^3P$ and the like. All of the foregoing can be incorporated into an RNA using the standard synthesis techniques disclosed herein.

As used herein, the term "therapeutically effective amount" shall be taken to mean a sufficient quantity of RNA aptamer, anticancer agent, delivery agent or pharmaceutical composition according to the present disclosure to reduce or inhibit the number of EpCAM expressing cancer stem cells and/or one or more symptoms of cancer. The skilled artisan will be aware that such an amount will vary depending upon, for example, the particular subject and/or the type or severity or level of disease. The term is not be construed to limit the present disclosure to a specific quantity of RNA aptamer.

As used herein, the term "treat" or "treatment" or "treating" shall be understood to mean administering a therapeutically effective amount of RNA aptamer, anticancer agent, delivery agent or pharmaceutical composition as disclosed herein and reducing or inhibiting at least one symptom of a clinical condition associated with or caused by cancer.

As used herein, the term "prevent" or "preventing" or "prevention" shall be taken to mean administering a therapeutically effective amount of RNA aptamer, anticancer agent, delivery agent or pharmaceutical composition according to the present disclosure and stopping or hindering or delaying the development or progression of at least one symptom of cancer.

As used herein, the term "specifically binds" shall be taken to mean that the RNA aptamer reacts or associates more frequently, more rapidly, with greater duration and/or with greater affinity with a particular cell or substance than it does with alternative cells or substances. For example, an RNA aptamer that specifically binds to a target protein binds that protein or an epitope or immunogenic fragment thereof with greater affinity, avidity, more readily, and/or with greater duration than it binds to unrelated protein and/or epitopes or immunogenic fragments thereof. It is also understood by reading this definition that, for example, a RNA aptamer that specifically binds to a first target may or may not specifically bind to a second target. As such, "specific binding" does not necessarily require exclusive binding or non-detectable binding of another molecule, this is encompassed by the term "selective binding". Generally, but not necessarily, reference to binding means specific binding. The specificity of binding is defined in terms of the comparative dissociation constants (Kd) of the aptamer for target as compared to the dissociation constant with respect to the aptamer and other materials in the environment or unrelated molecules in general. Typically, the Kd for the aptamer with respect to the target will be 2-fold, 5-fold, or 10-fold less than the Kd with respect to the target and the unrelated material or accompanying material in the environment. Even more preferably, the Kd will be 50-fold, 100-fold or 200-fold less.

The term "EpCAM+" or "EpCAM expressing cell" as used herein may be used interchangeably. The term encompasses cell surface expression of the CD133 antigen which can be detected by any suitable means. Reference to a cell being positive for a given marker means it may be either a low (lo or dim) or a high (bright, bri) expresser of that marker depending on the degree to which the marker is present on the cell surface, where the terms relate to intensity of fluorescence. The same applies in reference to the expression of CD44 and CD24 as measured by flow cytometry.

As used herein, the term "subject" shall be taken to mean any subject, including a human or non-human subject. The non-human subject may include non-human primates, ungulate (bovines, porcines, ovines, caprines, equines, buffalo and bison), canine, feline, lagomorph (rabbits, hares and pikas), rodent (mouse, rat, guinea pig, hamster and gerbil), avian, and fish. In one example, the subject is a human.

Aptamers

Several unique properties of aptamers make them attractive tools for use in a wide array of molecular biology applications, and as potential pharmaceutical agents. First, most aptamers bind to targets with high affinity, demonstrating typical dissociation constants in the pico- to nanomolar range. Binding sites for aptamers include clefts and grooves of target molecules resulting in antagonistic activity very similar to many currently available pharmaceutical agents. Second, aptamers are structurally stable across a wide range of temperature and storage conditions, maintaining the ability to form their unique tertiary structures. Third, aptamers can be chemically synthesised, in contrast to the expensive and work-intensive biological systems needed to produce monoclonal antibodies.

Without wishing to be bound by theory, RNA aptamers are generally preferred by many groups due to the theoretically higher affinity of RNA aptamers for their target proteins as well as the greater plasma stability of modified RNA than unmodified RNA.

Disclosed herein are RNA aptamer molecules that specifically bind to the EpCAM antigen which can be used for effective intracellular delivery of siRNA or ribozyme, chemotherapy drugs, radioisotopes, toxins and/or other agents bearing the antigen.

Aptamers are single stranded oligonucleotides or oligonucleotide analogs that bind to a particular target molecule, such as a protein or a small molecule. Thus, aptamers are the oligonucleotide analogy to antibodies. In general, aptamers comprise about 15 to about 100 nucleotides, preferably about 15 to about 40 nucleotides, and more preferably about 20 to about 40 nucleotides, in that oligonucleotides of a length that falls within these ranges can be prepared by conventional techniques. Optionally, aptamers can further comprise a minimum of approximately 6 nucleotides, preferably 10, and more preferably 14 or 15 nucleotides, that are necessary to effect specific binding. Aptamers of binding regions containing sequences shorter than 10, e.g., 6-mers, are feasible if the appropriate interaction can be obtained in the context of the environment in which the target is placed. Thus, if there is little interference by other materials, less specificity and less strength of binding can be required.

Aptamer binding is highly dependent on the secondary structure formed by the aptamer oligonucleotide. Both RNA and single stranded DNA (or analog) aptamers are known. See, for example, Burke et al (1996). J. Mol. Biol. 264:650-666; Ellington and Szostak (1990). Nature 346:818-22; Hirao et al (1998). Mol Divers. 4:75-89; Jaeger et al (1998). EMBO Journal 17:4535; Kensch et al (2000). J. Biol. Chem 275:18271-8; Schneider et al (1995). Biochemistry 34:9599-9610; and U.S. Pat. No. 5,773,598; U.S. Pat. No. 6,028,186; U.S. Pat. No. 6,110,900; U.S. Pat. No. 6,127,119; and U.S. Pat. No. 6,171,795.

Selection of Aptamers for a Given Target

Aptamers that bind to virtually any particular target can be selected by using an iterative process called SELEX™ (Systemic Evolution of Ligands by EXponential Enrichment). The process is described in, for example U.S. Pat. No. 5,270,163 and U.S. Pat. No. 5,475,096. The SELEX™ process is based on the unique insight that nucleic acids have sufficient capacity for forming a variety of two- and three-dimensional structures and sufficient chemical versatility available within their monomers to act as ligands (i.e., form specific binding pairs) with virtually any chemical compound, whether monomeric or polymeric. Molecules of any size or composition can serve as targets.

The SELEX™ process relies, as a starting point, upon a large library or pool of single stranded oligonucleotides comprising randomised sequences. The oligonucleotides can be modified or unmodified DNA, RNA, or DNA/RNA hybrids. In some examples, the pool comprises 100% random or partially random oligonucleotides. In other examples, the pool comprises random or partially random oligonucleotides containing at least one fixed sequence and/or conserved sequence incorporated within randomized sequence. In other examples, the pool comprises random or partially random oligonucleotides containing at least one fixed sequence and/or conserved sequence at its 5' and/or 3' end which may comprise a sequence shared by all the molecules of the oligonucleotide pool. Fixed sequences are sequences common to oligonucleotides in the pool which are incorporated for a preselected purpose such as, CpG motifs, hybridization sites for PCR primers, promoter sequences for RNA polymerases (e.g., T3, T4, T7, and SP6), restriction sites, or homopolymeric sequences, such as poly A or poly T tracts, catalytic cores, sites for selective binding to affinity columns, and other sequences to facilitate cloning and/or sequencing of an oligonucleotide of interest. Conserved sequences are sequences, other than the previously described fixed sequences, shared by a number of aptamers that bind to the same target.

The oligonucleotides of the pool preferably include a randomised sequence portion as well as fixed sequences necessary for efficient amplification. Typically, the oligonucleotides of the starting pool contain fixed 5' and 3' terminal sequences which flank an internal region of 30-50 random nucleotides. The randomised nucleotides can be produced in a number of ways including chemical synthesis and size selection from randomly cleaved cellular nucleic acids. Sequence variation in the test nucleic acids can also be introduced or increased by mutagenesis before or during the selection/amplification iterations.

The random sequence portion of the oligonucleotide can be of any length and can comprise ribonucleotides and/or deoxyribonucleotides and can include modified or non-natural nucleotides or nucleotide analogs (see for example U.S. Pat. No. 5,958,691, U.S. Pat. No. 5,660,985 and WO 92/07065). Random oligonucleotides can be synthesized from phosphodiester-linked nucleotides using solid phase oligonucleotide synthesis techniques well known in the art. See, for example, Froehler et al., (1986). Nucl. Acid Res. 14:5399-5467 and Froehler et al (1986) Tet. Lett. 27:5575-

5578. Random oligonucleotides can also be synthesized using solution phase methods such as triester synthesis methods. See, e.g., Sood et al (1977). Nucl. Acid Res. 4:2557 and Hirose et al (1978). Tet. Lett., 28:2449. Typical syntheses carried out on automated DNA synthesis equipment yield $10^{14}$-$10^{16}$ individual molecules, a number sufficient for most SELEX™ experiments.

The starting library of oligonucleotides may be generated by automated chemical synthesis on a DNA synthesiser. Partially random sequences can be created by adding the four nucleotides in different molar ratios at each addition step.

The starting library of oligonucleotides may be either RNA or DNA. In those instances where an RNA library is to be used as the starting library it is typically generated by transcribing a DNA library in vitro using T7 RNA polymerase or modified T7 RNA polymerases and purified. The RNA or DNA library is then mixed with the target under conditions favourable for binding and subjected to step-wise iterations of binding, partitioning and amplification, using the same general selection scheme, to achieve virtually any desired criterion of binding affinity and selectivity. More specifically, starting with a mixture containing the starting pool of nucleic acids, the SELEX™ method includes steps of: (a) contacting the mixture with the target under conditions favorable for binding: (b) partitioning unbound nucleic acids from those nucleic acids which have bound specifically to target molecules; (c) dissociating the nucleic acid-target complexes; (d) amplifying the nucleic acids dissociated from the nucleic acid-target complexes to yield a ligand-enriched mixture of nucleic acids; and (e) reiterating the steps of binding, partitioning, dissociating and amplifying through as many cycles as desired to yield highly specific, high affinity nucleic acid ligands to the target molecule. In those instances where RNA aptamers are being selected, the SELEX™ method further comprises the steps of: (i) reverse transcribing the nucleic acids dissociated from the nucleic acid-target complexes before amplification in step (d); and (ii) transcribing the amplified nucleic acids from step (d) before restarting the process.

Cycles of selection and amplification are repeated until a desired goal is achieved. Generally this is until no significant improvement in binding strength is achieved on repetition of the cycle. Typically, nucleic acid aptamer molecules are selected in a 5 to 20 cycle procedure.

A variety of nucleic acid primary, secondary and tertiary structures are known to exist. The structures or motifs that have been shown most commonly to be involved in non-Watson-Crick type interactions are referred to as hairpin loops, symmetric and asymmetric bulges, pseudoknots and myriad combinations of the same. Almost all known cases of such motifs suggest that they can be formed in a nucleic acid sequence of no more than 30 nucleotides. For this reason, it is often preferred that SELEX™ procedures with contiguous randomized segments be initiated with nucleic acid sequences containing a randomized segment of between about 20 to about 50 nucleotides.

The core SELEX™ method has been modified to achieve a number of specific objectives. For example, U.S. Pat. No. 5,707,796 describes the use of SELEX™ in conjunction with gel electrophoresis to select nucleic acid molecules with specific structural characteristics, such as bent DNA. U.S. Pat. No. 5,763,177 describes SELEX™ based methods for selecting nucleic acid ligands containing photo reactive groups capable of binding and/or photo-crosslinking to and/or photo-inactivating a target molecule. U.S. Pat. No. 5,567,588 and U.S. Pat. No. 5,861,254 describe SELEX™ based methods which achieve highly efficient partitioning between oligonucleotides having high and low affinity for a target molecule. U.S. Pat. No. 5,496,938 describes methods for obtaining improved nucleic acid ligands after the SELEX™ process has been performed. U.S. Pat. No. 5,705, 337 describes methods for covalently linking a ligand to its target Counter-SELEX™ is a method for improving the specificity of nucleic acid ligands to a target molecule by eliminating nucleic acid ligand sequences with cross-reactivity to one or more non-target molecules. Counter-SELEX™ is comprised of the steps of: (a) preparing a candidate mixture of nucleic acids; (b) contacting the candidate mixture with the target, wherein nucleic acids having an increased affinity to the target relative to the candidate mixture may be partitioned from the remainder of the candidate mixture; (c) partitioning the increased affinity nucleic acids from the remainder of the candidate mixture; (d) dissociating the increased affinity nucleic acids from the target; (e) contacting the increased affinity nucleic acids with one or more non-target molecules such that nucleic acid ligands with specific affinity for the non-target molecule(s) are removed; and (f) amplifying the nucleic acids with specific affinity only to the target molecule to yield a mixture of nucleic acids enriched for nucleic acid sequences with a relatively higher affinity and specificity for binding to the target molecule. As described above for SELEX™, cycles of selection and amplification are repeated as necessary until a desired goal is achieved.

In a representative example, an RNA aptamer is synthesized on a solid support column, using conventional techniques such as those described by Beaucage et al. (1981) Tetrahedr. Letters 22:1859-1862 and Sinha et al., (1984) Nucleosides and Nucleotides 3:157-171. The final DMT-group is removed from the resulting RNA aptamer. Alternately, if large-scale synthesis is used, the RNA aptamer can be made by scale-up of the solid support method or the RNA aptamer can be made by using solution phase techniques, particularly if the desired end-product is a relatively short oligonucleotide. A starting material for the synthesis process can be a 5'-non-tritylated RNA oligoribo-nucleotide or analog of the desired primary structure, which preferably can have protected bases, and which is preferably bound to a solid-support. Any conventionally used protecting groups can be used. Typically $N_6$-benzoyl is used for adenine, $N_4$-benzoyl for cytosine, $N_2$-isobutyryl for guanine and $N_2$-benzoyl for 2-amino purine. Other useful protecting groups include phenoxyacetyl (PAC) and t-butoxyacetyl (TAC). Conveniently, the more base labile protection groups should be used for the synthesis of the RNA aptamer; those of ordinary skill in the art know these groups. Such groups can help to prevent hydrolysis of the generated tri- or diphosphates, which are generally quite stable under basic conditions, but could be subject to some hydrolysis. Other envisioned modifications are disclosed in U.S. Pat. No. 6,011,020, and include but are not limited to the incorporation of bioavailability enhancing molecules such as PEG or cholesterol via a covalent linkage.

In addition, nucleoside analogs such as 2'-deoxy, 2'-halo, 2'-amino (not substituted or mono- or disubstituted), 2'-mono, di- or trihalomethyl, 2'-O-alkyl, 2'-O-halo-substituted alkyl, 2'-alkyl, azido, phosphorothioate, sulfhydryl, methylphosphonate, fluorescein, rhodamine, pyrene, biotin, xanthine, hypoxanthine, 2,6-diamino purine, 2-hydroxy-6-mercaptopurine and pyrimidine bases substituted at the 6-position with sulfur or 5 position with halo or $C_{1-5}$ alkyl groups, abasic linkers, 3'-deoxy-adenosine as well as other available "chain terminator" or "non-extendible" analogs (at the 3'-end of the RNA), and the like can be incorporated during the RNA synthesis. Further, various labels such as $^{32}$P or $^3$P and the like can likewise be incorporated during the synthesis, resulting in novel RNA analogs produced by this process. Other envisioned modifications are disclosed in U.S. Pat. No. 6,011,020, and include but are not limited to the incorporation of 3' caps, such an inverted DT cap, or an inverted abasic cap, or combination thereof.

Binding Affinity of Aptamers

The binding affinity describes the measure of the strength of the binding or affinity of molecules to each other. Binding affinity of the aptamer herein with respect to targets and other molecules is defined in terms of $K_d$. The dissociation constant can be determined by methods known in the art and can be computed even for complex mixtures by methods such as those, for example, set forth in Cacecci, M., et al., *Byte* (1984) 9:340-362. Examples of measuring dissociation constants are described for example in U.S. Pat. No. 7,602, 495 which describes surface Plasmon resonance analysis, U.S. Pat. No. 6,562,627, U.S. Pat. No. 6,562,627, and US 2012/00445849. In another example, the $K_d$ is established using a double-filter nitrocellulose filter binding assay such as that disclosed by Wong and Lohman, (1993). *Proc. Natl. Acad. Sci. USA* 90, 5428-5432.

It has been observed, however, that for some small oligonucleotides, direct determination of $K_d$ is difficult, and can lead to misleadingly high results. Under these circumstances, a competitive binding assay for the target molecule or other candidate substance can be conducted with respect to substances known to bind the target or candidate. The value of the concentration at which 50% inhibition occurs ($K_i$) is, under ideal conditions, equivalent to $K_d$. However, in no event will a $K_i$ be less than $K_d$. Thus, determination of $K_i$, in the alternative, sets a maximal value for the value of $K_d$. Under those circumstances where technical difficulties preclude accurate measurement of $K_d$, measurement of K can conveniently be substituted to provide an upper limit for $K_d$. A $K_i$ value can also be used to confirm that an aptamer of the present binds a target.

Improving Aptamer Stability

One potential problem encountered in the use of nucleic acids as therapeutics in that oligonucleotides in their phosphodiester form may be quickly degraded in body fluids by intracellular and extracellular enzymes such as endonucleases and exonucleases before the desired effect is manifest. The present disclosure also includes RNA analogs as described herein and/or additional modifications designed to improve one or more characteristics of the RNA aptamer such as protection from nuclease digestion.

Oligonucleotide modifications contemplated in the present disclosure include, but are not limited to, those which provide other chemical groups that incorporate additional charge, polarizability, hydrophobicity, hydrogen bonding, electrostatic interaction, and fluxionality to the nucleic acid ligand bases or to the nucleic acid ligand as a whole.

Modifications to generate oligonucleotides which are resistant to nucleases can also include one or more substitute internucleotide linkages, altered sugars, altered bases, or combinations thereof. Such modifications include 2'-position sugar modifications, 5-position pyrimidine modifications, 8-position purine modifications, modifications at exocyclic amines, substitution of 4-thiouridine, substitution of 5-bromo or 5-iodo-uracil, backbone modifications, phosphorothioate or alkyl phosphate modifications, methylations, and unusual base-pairing combinations such as the isobases isocytidine and isoguanosine; 3' and 5' modifications such as capping; conjugation to a high molecular weight, non-immunogenic compound; conjugation to a lipophilic compound; and phosphate backbone modification.

In one example, the non-immunogenic, high molecular weight compound conjugated to the aptamer of the present disclosure is polyalkylene glycol, preferably polyethylene glycol. In one example, the backbone modification comprises incorporation of one or more phosphorothioates into the phosphate backbone. In another example, the aptamer of the present disclosure comprises the incorporation of fewer than 10, fewer than 6, or fewer than 3 phosphorothioates in the phosphate backbone.

Utility of the Aptamers

The RNA aptamer molecules of the present disclosure can be used as affinity ligands to separate and purify target molecules (e.g. EpCAM bearing cancer stem cells), as probes to trace, monitor, detect and quantitate target molecules (e.g. EpCAM bearing cancer stem cells), or to block, allow, activate or catalyse reactions that are physiologically relevant to achieve therapeutic effect. They can act as pharmaceutical agent, bind to a specific target and direct specific molecules to a desired site.

The RNA aptamer molecules of the present disclosure can be used in in vitro processes, for example affinity purification mixtures to purify target molecules (e.g. EpCAM bearing cancer stem cells). The aptamers are ideal for chromatographic separations of target molecules (e.g. EpCAM bearing cancer stem cells) from contaminants and for purifying target molecules from cell cultures or cell extracts.

In one example, the RNA aptamer molecules of the present disclosure can be used as a capture agent to bind or immobilise a target (e.g. EpCAM bearing cancer stem cells) to a solid support. The solid support can be comprised of substrates having the structure and composition commonly associated with filters, wafers, wafer chips, membranes and thin films. However, it is contemplated that the solid support may be comprises of substrates including, but not limited to resins, affinity resins, magnetic or polymer beads, or any diagnostic detection reagent, to capture or immobilise reagents for diagnostic, detection or quantitative studies, The solid supports may comprise any material depending of the desired use, including but not limited to glass, metal surfaces and materials such as steel, ceramic or polymeric materials such as polyethylene, polypropylene, polyamide, and polyvinylidenefluoride etc or combinations thereof.

Isolation and Purification of EpCAM Expression Cancer Stem Cells

The best known example of adult cell renewal by the differentiation of stem cells is the hematopoietic system. Developmentally immature precursors such as hematopoietic stem cells and progenitor cells respond to molecular signals to gradually form the varied blood and lymphoid cell types. Stem cells are also found in other tissues, including epithelial tissues and mesenchymal tissues. Cancer stem cells may arise from any of these cell types, for example, as a result of genetic damage in normal stem cells or by the dysregulated proliferation of stem cells and/or differentiated cells.

Cancer stem cells may be derived from any cancer comprising tumorigenic stem cells, i.e. cells having an ability to proliferate extensively or indefinitely, and which give rise to the majority of cancer cells. Within an established tumor, most cells have lost the ability to proliferate extensively and form new tumors, and a small subset of cancer stem cells proliferate to thereby regenerate the cancer stem cells as well as give rise to tumor cells lacking tumorigenic potential. Cancer stem cells may divide asymmetrically and symmetrically and may show variable rates of proliferation. Cancer stem cell may include transit amplifying cells or progenitor cells that have reacquired stem cell properties.

Representative cancers from which stem cells may be isolated include cancers characterised by solid tumors, including for example fibrosarcoma, myxosarcoma, liposarcoma, chondrosarcoma, osteogenic sarcoma, chordoma, angiosarcoma, endotheliosarcoma, lymphangiosarcoma, synovioma, lymphangioendotheliosarcoma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma and retinoblastoma.

Additional representative cancers from which stem cells can be isolated or enriched according to the present disclosure include hematopoietic malignancies, such as B cell lymphomas and leukemias, including low grade/Follicular non-Hodgkin's lymphoma (NHL), small lymphocytic (SL) NHL, intermediate grade/follicular NHL, intermediate grade diffuse NHL, high grade immunoblastic NHL, high grade small non-cleaved cell NHL, bulky disease NHL and Waldenstrom's Macroglobulinemia, chronic leukocytic leukemia, acute myelogenous leukemia, chronic myelogenous leukemia, lymphoblastic leukemia, lymphocytic leukemia, monocytic leukemia, myelogenous leukemia and promyelocytic leukemia.

Cancer stem cells bearing EpCAM may be selected using the aptamer molecules as described herein. For example, aptamers which are coupled to fluorescent dyes can be used for the positive selection of cancer stem cells. EpCAM is also known to be expressed in some normal cells. However, EpCAM expression is thought to be upregulated in cancer stem cells. Cancer stem cell markers are typically expressed at a level that is at least about 5-fold greater than differentiated cells of the same origin or non-tumorigenic cells, for example, at least about 10-fold greater, or at least about 15-fold greater, or at least about 20-fold greater, or at least about 50-fold greater, or at least about 100-fold greater. The selection process may also include negative selection markers which can be used for the elimination of those cancer cells in the population that are not cancer stem cells.

It will be understood that in performing the present disclosure, separation of cells bearing EpCAM can be effected by a number of different methods. For example, the RNA aptamer of the present disclosure may be attached to a solid support to allow for a crude separation. Various techniques of different efficacy may be employed depending upon efficiency of separation, associated cytotoxicity, ease and speed of performance and necessity for sophisticated equipment and/or technical skill. Procedures for isolation or purification may include, but are not limited to, magnetic separation using aptamer-coated magnetic beads, affinity chromatography and "panning" with aptamer attached to a solid matrix. Techniques providing accurate isolation or purification include but are not limited to FACS. Methods for preparing FACS will be apparent to the skilled artisan.

Enrichment of EpCAM Expressing Cancer Stem Cells

In one example, the RNA aptamer molecules of the present disclosure are enriched from a biological sample obtained from a subject. Typically the subject will be one which has a tumor or is suspected of having a tumor containing cancer stem cells. The term "enriched" or "enrichment" or variations thereof are used herein to describe a population of cells in which the proportion of one particular cell type (i.e. cancer stem cells) is increased when compared with an untreated population of the cells (e.g. cells in the sample).

In one example, a population enriched for cancer stem cells comprises at least about 0.1%, or 0.5% or 1% or 2% or 5% or 10% or 15% or 20% or 25% or 30% or 50% or 75% EpCAM bearing cancer stem cells. In this regard, the term "enriched cell population comprising cancer stem cells" will be taken to provide explicit support for the term "population of cells comprising X % cancer stem cells, wherein X % is a percentage as recited herein.

In one example, the population of cells is enriched from a cell preparation comprising EpCAM$^+$ cells in a selectable form. In this regard, the term "selectable form" will be understood to mean that the cells express a marker (e.g. a cell surface marker) permitting selection of EpCAM bearing cells.

Diagnosis of Cancer Using Aptamer Molecules

The RNA aptamer molecules of the present disclosure can be used in vitro for diagnostic purposes to determine the presence of cancer stem cells in malignant tissue. The method involves examining a biological sample for the presence of EpCAM$^+$ cancer stem cells. For example, the biological sample can be contacted with a labelled RNA aptamer of the present disclosure and the ability of the RNA aptamer to specifically bind to the cells in the sample is determined. Binding by the aptamer indicates the presence of an EpCAM bearing cell. In one example the EpCAM bearing cell is a cancer stem cell.

The RNA aptamer of the present disclosure can also be used to localise a EpCAM$^+$ tumor in vivo by administering to a subject an isolated RNA aptamer of the present disclosure which is labelled with a reporter group which gives a detectable signal. Bound aptamers can then be detected using flow cytometry, microscopy, external scintigraphy, emission tomography, optical imaging or radionuclear scanning. The method can be used to stage a cancer in a subject with respect to the extent of the disease and to monitor changes in response to therapy.

Detection of cancer stem cells can be facilitated by coupling the RNA aptamer to a detectable label. Examples of detectable labels include various enzymes, prosthetic groups, fluorescent materials, luminescent materials, bioluminescent materials, electron dense labels, labels for MRI, and radioactive materials. Examples of suitable enzymes include horseradish peroxidise, alkaline phosphatise, β-galactosidase, or acetylcholinesterase. Examples of suitable prosthetic group complexes include streptavidin/biotin and avidin/biotin. Examples of suitable fluorescent materials include umbellifone, fluorescein isothiocyanate, rhodamine, dichlorotriazinylamine fluorescein, dansyl chloride or phycoerythrin. An example of a luminescent material includes luminol. Examples of bioluminescent materials include luciferase, luciferin, and aequorin, and examples of suitable radioactive material include $^{125}$I, $^{131}$I, $^{35}$S, $^{18}$F, $^{64}$Cu, $^{94m}$Tc, $^{124}$I, $^{11}$C, $^{13}$N, $^{15}$O, $^{68}$Ga, $^{86}$Y, $^{82}$Rb or $^{3}$H.

Labelling at the 3' end of the aptamer can be achieved, for example by templated extension using Klenow polymerase, by T4 RNA ligase-mediated ligation and by terminal deoxynucleotidyl transferase. Labelling at the 5' end can be achieved by the supplementation of the in vitro transcription mix with an excess of GTP-β-S, the thiol of which can then be used to attach biotin. In addition, direct chemical conjugation of a suitable group(s) to either 5'- or 3'-end can be used to label the aptamers.

Anticancer Agent of the Present Disclosure

The RNA aptamer molecules of the present disclosure can be conjugated to a moiety and used to direct the moiety to EpCAM+ cells, preferably cancer stem cells. Examples of moieties include toxins, radionuclides, or chemotherapeutic agents which can be used to kill cancer stem cells.

The RNA aptamer can be fused to the moiety, e.g. the toxin, either by virtue of the moiety and aptamer being chemically synthesised, or by means of conjugation, e.g. a non-peptide covalent bond, e.g. a non-amide bond, which is used to join separately produced RNA aptamer and the moiety. Alternatively, the RNA aptamer and moiety may be joined by virtue of a suitable linker peptide.

Useful toxin molecules include peptide toxins, which are significantly cytotoxic when present intracellularly. Examples of toxins include cytotoxins, metabolic disrupters (inhibitors and activators) that disrupt enzymatic activity and thereby kill cancer stem cells, and radioactive molecules that kill all cells within a defined radius of the effector portion. A metabolic disrupter is a molecule, e.g. an enzyme or a cytokine that changes the metabolism of a cell such that is normal function is altered. Broadly, the term toxin includes any effector that causes death to a tumor cell.

Many peptide toxins have a generalised eukaryotic receptor binding domain; in these instances the toxin must be modified to prevent killing cells not bearing EpCAM (e.g. to prevent killing cells not bearing EpCAM but having a receptor for the unmodified toxin). Such modifications must be made in a manner that preserves the cytotoxic function of the molecule. Potentially useful toxins include, but are not limited to diphtheria toxin, cholera toxin, ricin, 0-Shiga-like toxin (SLT-I, SLT-II, SLT-II$_V$), LT toxin, C3 toxin, Shiga toxin pertussis toxin, tetanus toxin, *Pseudomonas* exotoxin, alorin, saponin, modeccin and gelanin. Other toxins include tumor necrosis actor alpha (TNF-alpha) and lymphotoxin (LT). Another toxin which has antitumor activity is calicheamicin gamma 1, a diyne-ene containing antitumor antibiotic with considerable potency against tumors (Zein N et al (1988). Science 240:1198-201).

As an example, diphtheria toxin (which sequence is known) can be conjugated to the RNA aptamer molecules of the present disclosure. The natural diphtheria toxin molecule secreted by *Corynebacterium* diptheriae consist of several functional domains that can be characterised, starting at the amino terminal end of the molecule, as enzymatically-active fragment A (AA 1-193) and fragment B (AA 194-535) which includes a translocation domain and a generalised cell binding domain (AA 475-535).

The RNA aptamer and the toxin moiety can be linked in any of several ways which will be known to persons skilled in the art. For example, a method of conjugating an RNA aptamer to a toxin (gelonin) is described in Chu T C et al. (2006) Cancer Res 6(12)5989-5992.

The moiety can also be a modulator of the immune system that either activates or inhibits the body's immune system at the local level. For example, cytokines e.g. lymphokines such as IL-2, delivered to a tumor can cause the proliferation of cytotoxic T-lymphocytes or natural killer cells in the vicinity of the tumor.

The moiety or reporter group can also be a radioactive molecule, e.g. a radionucleotide, or a so-called sensitizer, e.g. a precursor molecule that becomes radioactive under specific conditions, e.g. boron when exposed to a bean of low-energy neutrons, in the so-called "boron neutron capture therapy" (BNCT) as described in Barth et al. (1990). Scientific American Oct 1990:100-107. Compounds with such radioactive effector portions can be used both to inhibit proliferation of cancer stem cells in the tumor and to label the cancer stem cells for imaging purposes.

Radionucleotides are single atom radioactive molecules that can emit either α, β, or γ particles. Alpha particle emitters are preferred to β, or γ particle emitters, because they release far higher energy emissions over a shorter distance, and are therefore efficient without significantly penetrating, and harming, normal tissues. Suitable a particle emitting radionuclides include $^{211}$At, $^{212}$Pb, and $^{212}$Bi.

The radioactive molecule must be tightly linked to the aptamer either directly or by a bifunctional chelate. This chelate must not allow elution and thus premature release of the radioactive molecule in vivo. Waldmann, Science, 252: 1657-62 (1991). As an example, to adapt BNCT to the present invention, a stable isotope of boron, e.g., boron 10, can be selected as the antitumor moiety or effector portion of the compound. The boron will be delivered to and concentrates in or on the tumor cells by the specific binding of the aptamer to the cancer stem cell. After a time that allows a sufficient amount of the boron to accumulate, the tumor can be imaged and irradiated with a beam of low-energy neutrons, having an energy of about 0.025 eV. While this neutron irradiation, by itself, causes little damage to either the healthy tissue surrounding the tumor, or the tumor itself, boron 10 (e.g., on the surface of a tumor cell) will capture the neutrons, thereby forming an unstable isotope, boron 11. Boron 11 instantly fissions yielding lithium 7 nuclei and energetic a particles, about 2.79 million Ev. These heavy particles are a highly lethal, but very localized, form of radiation, because particles have a path length of only about one cell diameter (10 microns).

Delivery Agent of the Present Disclosure

The RNA aptamer molecules of the present disclosure can be used for siRNA or ribozyme delivery into cells. Examples of suitable siRNA or ribozyme will depend upon the circumstances. Examples of siRNAs or ribozymes that are suitable for use according to the present disclosure include those which target ATP binding cassette membrane transporters, stemness genes (Bmi-1, Notch 1, Sox 2, Oct-4, Nanog, β-catenin, Smo, nestin, ABCG2, Wnt2 and SCF, etc), GAPDH (glyceraldehyde 3-phosphate dehydrogenase), and survivin.

By way of example, this has been demonstrated in the prior art using an anti-PSMA aptamer. Based on the knowledge that PSMA is internalised via clathrin-coated pits to endosome, it was postulated that the anti-PSMA aptamer would carry the attached siRNA to the cells that express PSMA, and the aptamer-siRNA bound to the PSMA protein would gain access to the cell via internalisation. Next, the siRNA portion would undergo processing by the Dicer complex and feed into the RNA-Induced Silencing Complex (RISC)-mediated gene-silencing pathway. Three groups have utilised different strategies to accomplish this. Chu et al (2006) Nucleic Acids Res 34, e73 describes a biotin-streptavidin bridge mediated conjugation method to assemble the anti-PSMA aptamer and the siRNA. McNamara et al. (2006) Nat Biotechnol 24, 1005-1015 used a "RNA-only" aptamer-siRNA chimera approach to link the aptamer and the siRNA. In a subsequent study by Wullner et al (2008). Curr. Cancer Drug Targets 8:554-565, the authors used the anti-PSMA aptamer to deliver Eukaryotic Elongation Factor 2 (EEF2) siRNA to PSMA-positive prostate cancer cells, Bivalent PSMA aptamers were used for this purpose. The authors demonstrated that, compared to the monovalent anti-PSMA-siRNA chimera, the gene knockdown potency of the bivalent aptamer-construct was superior.

The RNA aptamer molecules of the present disclosure can also be used to deliver cargo into EpCAM$^+$ cancer stem cells in a variety of solid tumours. Gelonin is a ribosomal toxin that can inhibit the process of protein synthesis and is cytotoxic. However, it is membrane impermeable and needs an usher for its cellular entry. Thus, the RNA aptamer molecules of the present disclosure can be utilised to deliver membrane impermeable toxic payload to cancer stem cells.

Tumor resistance to cytotoxic chemotherapeutic agents is due in part to insufficient delivery to and uptake, and more importantly, efflux by cancer cells. Biodegradable nanoparticle (NP) derived from poly(D,L-lactic-co-glycolic acid) PLGA were used to address this problem as described in Dhar et al (2008) Proc. Natl. Acad. Sci. USA 105:17356-17361. Briefly, cisplatin was converted to its pro-drug, Pt(IV) compound, by introducing two alkyl chains. This increased the hydrophobicity of the compound and eased the process of its packaging within the hydrophobic core of the NP. Polyethylene glycol (PEG) was used as a copolymer during the nanoprecipitation step to synthesise the PLGA-PEG nanoparticle. The PLGA-PEG-NP surface was decorated with a PSMA (prostate specific membrane antigen) aptamer. The NP underwent endocytosis when incubated with LNCaP cells, and the alkylated pro-drug was converted to cisplatin by the cytosolic reduction process.

The present disclosure also extends to the use of the RNA aptamer molecules as simultaneous drug delivery and imaging agents. This can be achieved by conjugating the aptamer to the surface of a fluorescent quantum dot (QD). Next, the QD-aptamer conjugate is incubated with Dox to form the OD-aptamer-Dox nanoparticle. Both Dox and QD are fluorescent molecules. However, due to their proximity in the QD-aptamer-Dox nanoparticle, they quench each other's fluorescence by a bi-fluorescence resonance energy transfer (FRET) mechanism. Thus, the QD-aptamer-Dox nanoparticle is non-fluorescent. However, internalisation of the QD-aptamer-Dox nanoparticle via PSMA-mediated endocytosis in prostate cancer cells causes the release of Dox from the QD-aptamer-Dox nanoparticles, that results in the recovery of fluorescence by both Dox and QD.

Pharmaceutical Compositions

In one example of the present disclosure the RNA aptamer, anticancer agent or drug delivery agent according to the present disclosure is administered in the form of a composition comprising a pharmaceutically acceptable carrier and/or excipient. The choice of excipient or other elements of the composition can be adapted in accordance with the route and device used for administration.

The terms "carrier" and "excipient" refer to compositions of matter that are conventionally used in the art to facilitate the storage, administration, and/or the biological activity of an active compound (see, e.g., Remington's Pharmaceutical Sciences, 16th Ed., Mac Publishing Company (1980). A carrier may also reduce any undesirable side effects of the active compound. A suitable carrier is, for example, stable, e.g., incapable of reacting with other ingredients in the carrier. In one example, the carrier does not produce significant local or systemic adverse effect in recipients at the dosages and concentrations employed for treatment.

Suitable carriers for the present disclosure include those conventionally used, e.g. water, saline, aqueous dextrose, lactose, Ringer's solution a buffered solution, hyaluronan and glycols are exemplary liquid carriers, particularly (when isotonic) for solutions. Suitable pharmaceutical carriers and excipients include starch, cellulose, glucose, lactose, sucrose, gelatin, malt, rice, flour, chalk, silica gel, magnesium stearate, sodium stearate, glycerol monostearate, sodium chloride, glycerol, propylene glycol, water, ethanol, and the like.

Other general additives such as anti-oxidative agent, buffer solution, bacteriostatic agent etc can be added. In order to prepare injectable solutions, pills, capsules, granules, or tablets, diluents, dispersing agents, surfactants, binders and lubricants can be additionally added.

The anticancer agent or drug delivery agent containing the RNA aptamer of the present invention can be administered parentally (for example, intravenous, hypodermic, local or peritoneal injection). The effective dosage of the anticancer agent can be determined according to weight, age, gender, health condition, diet, administration frequency, administration method, excretion and severity of a disease. In one example, the anticancer agent or drug delivery agent contains the RNA aptamer by 10-95 weight %. In another example, the anticancer agent or drug delivery agent contains the RNA aptamer by 25-75 weight %.

The administration frequency may be one to several times a day.

In one example, the effective intracellular content of the RNA aptamer is approximately 1 nM to 1000 nM. In another example, the effective intracellular content of the RNA aptamer is preferably 100 nM to 500 nM. However, the dosage of the aptamer could be under or more than the above range.

Combinations of Aptamers

The isolated RNA aptamer molecule(s) of the present disclosure can be used alone or in combination with one or more additional RNA aptamers according to any method disclosed herein. In one example, the RNA aptamer molecule(s) of the present disclosure can be combined with an RNA aptamer that facilitates the detection, purification or enrichment of cancer stem cells. In one example, the additional RNA aptamer is one which specifically binds to CD133$^+$ cells. In one example, the additional RNA aptamer comprises the sequence 5'-CCCUCCUACAUAGGG-3' (SEQ ID NO:4). In another example, the additional RNA aptamer comprises the sequence 5'-CAGAACGUAUAC-UAUUCUG-3' (SEQ ID NO:5).

Kits

The present disclosure also provides diagnostic kits for carrying out the methods disclosed herein. In one example, the diagnostic kit includes the RNA aptamer or the diagnostic agent as described herein for detecting EpCAM expressing cells (e.g. cancer stem cells).

The kit may also include ancillary agents such as buffering agents and stabilising agents. The diagnostic kit may further include agents for reducing background interference, control reagents and an apparatus for conducting a test. Instructions on how to use the diagnostic kit are generally also included.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

EXAMPLES

Methods

Aptamers

Aptamers against human EpCAM were generated and characterised as previously described (Shigdar S et al (2011). Cancer Sci 102:991-998). Aptamer DT3 and control aptamer were described previously (Shigdar S et al, supra), while aptamer 23 is a 19 base nucleotide with a near-infrared fluorescent dye, TYE 665, conjugated to its 5' end. This aptamer was characterised using the same methods as for the inventors previous aptamers (Shigdar S et al, supra).

Cell Lines and Culture and Xenograft Models

The cell lines of human origin used in this study were purchased from American type Culture Collection. They were glioblastoma U118-MG; breast carcinoma MCF-7, MDA-MB-231 and T47D; and colorectal adenocarcinoma HT-29. Cells were grown and maintained in culture with Dulbecco's Modified Eagle medium (DMEM) (Invitrogen, Victoria, Australia) supplemented with 10% fetal calf serum (MCF-7, T47D, HT-29, and U118-MG), or Roswell Park Memorial Institute 1640 (RPMI 1640) (Invitrogen) with 10% fetal calf serum (MDA-MB-231). Cells were maintained at 37 °C in a humidified atmosphere containing 5% $CO_2$. For xenograft studies, single cell suspensions were harvested by trypsinisation, washed with PBS and resuspended in 0.1 mL of PBS for implantation in BALB/c-Foxn1 $^{nu}$ female mice. Once tumours had reached approximately 5-8 $mm^3$, they were excised and fixed in 10% neutral buffered formalin prior to processing and embedding. All animal procedures were approved by Deakin University Animal Welfare Committee, and in accordance with the Australian Code of Practice for the Care and Use of Animals for Scientific Purposes.

Immunohistochemistry

Sections from each of the xenograft tumours were cut at 4 μm onto polylysine coated slides prior to deparaffinisation with Histoclear and rehydration through graded ethanol. Heat induced antigen retrieval was performed in a microwave oven using Tris-EDTA buffer (10 mM Tris, 1 mM EDTA, 0.05% Tween 20, pH 9.0) for 20 min and the slides were allowed to cool prior to blocking with 0.1 mg/mL tRNA, 0.1 mg/mL salmon sperm DNA and 1 mg/mL bovine serum albumin (BSA) in phosphate buffered saline (PBS) for 20 min. Following the blocking step, slides were washed in PBS containing 0.1% Tween 20 twice for 2 min prior to incubation with either aptamer or antibody. Aptamers were prepared as previously described (Shigdar S et al, supra). Briefly, aptamers were heated to 85° C. for 5 min, allowed to cool to room temperature for 10 min and then heated at 37° C. for 15 min. Slides were incubated with aptamers at 100 nM concentration in a solution of PBS containing 5 mM $MgCl_2$, 0.1 mg/mL tRNA, 1 mg/mL BSA, 10% dextran sulphate and 500 μg/mL heparin for 15 min at 37° C. The slides were then washed three times for 5 min each prior to incubation with Bisbenzimide Hoechst 33342 (3 μg/mL) for 10 min. Slides were then mounted using VECTASHIELD and coverslipped prior to visualisation using a Fluoview FV10i laser scanning confocal microscope. All images used for direct comparison were taken with identical exposure parameters and are presented without any digital contrast alteration or background subtraction. Antibody staining was performed using the anti-EpCAM antibody 323/A3 (ab8601, Abcam). Slides were washed and blocked following the same protocol as previously described prior to antibody staining. The antibody was prepared at a concentration of 10 μg/mL and the slides were incubated overnight at 4° C. Slides were then washed three times for 5 min followed by incubation with a goat-anti-mouse IgG AlexaFluor 647 conjugate (Invitrogen) at a concentration of 10 μg/mL for 2 h prior to washing, staining with Bisbenzimide Hoechst 33342, and coverslipping. Negative control slides were performed by replacing the primary antibody with PBS. Additionally, slides were stained with haematoxylin and eosin as well as the anti-EpCAM antibody, BerEP4, at St John of God Pathology Laboratory, Geelong, following their standard protocols.

Flow Cytometry Analysis

Cells were harvested at 80% confluence with trypsin digestion and resuspended in washing buffer (DPBS with 5 mM $MgCl_2$) and enumerated. Following centrifugation (1000×g for 5 min), the cell pellet was resuspended in assay buffer (DPBS supplemented with 5 mM $MgCl_2$, 0.1 mg/ml tRNA, 0.1 mg/ml salmon sperm DNA, 0.2% [w/v] sodium azide, and 5% FCS) and diluted to $1×10^6$/mL. The blocking step was carried out at 4'C. The binding of the aptamers was carried out at 37'C for 30 min or 4'C for 1 h, with the final concentration of magnesium chloride being 2.5 mM in all binding assays.

To confirm aptamer binding to the target protein, RNA from iterative rounds were labelled at the 3'-ends with fluorescein isothiocyanate (FITC) according to a previously described method (Willkomm & Hartmann (2005). Weinheim, Wiley-VCH GmbH & Co. KGaA 1:86-94). Amber tubes were used throughout to minimise photo-bleaching. Briefly, samples were oxidized with sodium periodate. The oxidation was terminated with the addition of 10 mM ethylene glycol, followed by ethanol precipitation. FITC was added at a 30-molar excess, and the reaction was completed overnight at 4° C. One μM of FITC-labelled RNA was incubated with trypsinised $5×10^5$ Kato III or U118-MG cells in 100 μl binding buffer (DPBS supplemented with 5 mM $MgCl_2$, 0.1 mg/ml tRNA, 0.1 mg/ml salmon sperm DNA) for 1 h on ice, followed by washing three times and resuspension in 300 μL of assay buffer. Fluorescent intensity was determined with a FACS Canto II flow cytometer (Becton Dickinson) by counting 50,000 events each sample. The FITC-labelled RNA from the unselected library was used to determine non-specific binding. The binding for each round was calculated after subtracting the mean fluorescence intensity of the binding of round zero RNA to target cells as well as that for binding to negative control cells according to a method described by Ellington and colleagues (Li et al. (2009). J. Proteome Res 8:2438-48). The dead cells were gated and excluded from the analyses by staining with 2.5 μg/ml propidium iodide and 0.5 mg/ml RNase A in PBS.

Confocal Microscopy

Twenty-four hours prior to labelling, cells were seeded at a density of 75,000 cells per $cm^2$ in a glass-bottom 8-chamber slide (Lab-Tek II, Nunc). DY647-Ep23 and the control aptamer were prepared in the same manner as for flow cytometry. Following removal of media, cells were incubated in assay buffer at 37'C for 15 mins, and washed twice prior to incubation with 100 nM aptamer with 2.5 $mgCl_2$ for 30 min at 37 °C. Bisbenzimide Hoechst 33342 (3 μg/mL) (Sigma) was added to the cells during the final 15 mins of incubation. The aptamer solution was removed and the cells washed 3 times for 5 min each in binding buffer prior to visualisation using a FluoView FV10i laser scanning confocal microscope (Olympus).

Inhibition of Endocytosis

This was performed essentially as described for confocal microscopy with minor modifications. Briefly, cells were pre-treated with either a potassium-depleted (50 mM Hepes, 140 mM NaCl, 2.5 mM MgCl$_2$, and 1 mM CaCl$_2$) or a hypertonic buffer (potassium-depleted buffer containing 3 mM KCl and 450 mM sucrose) for 1 hr at 37° C. These buffers were also used in the incubation step with aptamers and all rinsing steps. The effectiveness of these treatments in inhibiting endocytosis was verified by qualitatively characterising the internalisation of human transferrin conjugated to Alexa Fluor 488 (Invitrogen). Transferrin (5 μg/mL) was added to the cells following pre-treatment followed by a 30 min incubation at 37° C. The cells were washed three times in their respective buffers and visualised using the FluoView FV10i confocal microscope.

Colocalisation of Aptamers with Transferrin.

T47D, MCF7, MDA-MB-231, HT29 and U118MG cells were prepared as previously described for confocal microscopy. Following removal of media, cells were incubated in blocking buffer containing 5% (v/v) serum at 37° C. for 15 min, washed twice in binding buffer prior to incubation with 200 nM aptamer for 30 min at 37° C. The aptamer solution was removed and the cells washed 3 times for 5 min each in binding buffer. Transferrin were then added to the cells and incubated for 2 hours prior to Bisbenzimide Hoechst 33342 (3 μg/mL) (Sigma) being added to the cells during the final 15 mins of incubation. The cells washed 3 times for 5 min each in binding buffer prior to visualisation using a FluoView FV10i laser scanning confocal microscope.

EpCAM Aptamer

Human EpCAM cDNA was purchased from Invitrogen and cloned into a mammalian expression vector, pcDNA 3.1/V5-His-TOPO. The recombinant 6× Histine-tagged EpCAM was transiently expressed in HEK293T and the total cell lysate was prepared as described previously (Yeong S S et al. (2006) J Biol Chem 281(41):30768-81). Each well in the DELFIA anti-mouse-IgG coated plate (PerkinElmer, Cat. No. #4007-0010) was incubated with 1 μg of anti-His monoclonal antibody in binding buffer (Dulbecco's phosphate buffered saline (DPBS) containing 5 mM MgCl$_2$, 0.1 mg/mL tRNA and 0.1 mg/mL Salmon sperm DNA) for 1 h and blocked with SuperBlock (Pierce) for 1 h at 23° C. followed by extensive washing with binding buffer. The cell lysate containing the recombinant EpCAM was added to the wells, incubated for 1 h at 37° C. followed by six washes with binding buffer. The EpCAM strips were kept at 4° C. in a moist environment until use.

Aptamer Truncation

To generate the truncated aptamers of the present disclosure, the sense and antisense DNA oligonucleotides of desired sequence were synthesised. EpDT1 (1$^{st}$ Truncation) derived from a sense oligonucleotide, 5'-TAATACGACTCACTATAGGTCCGTAGTTCTGGC TGACTGGTTACCCGGTCGTACAGCTCG-3' (SEQ ID NO:6), and antisense oligonucleotide, 5'-CGAGCTGTAC-GACCGGGTA ACCAGTCAGCCAGAACTACGGAC-CTATAGTGAGTCGTATTA-3' (SEQ ID NO:7); EpDT3 (the third truncation) was derived from a sense oligonucleotide: 5'-TAATACGACTCACTATAGCGACTGGTTACCCG GTCG-3' (SEQ ID NO:8) and an antisense oligonucleotide, 5'-CGACCGGGTAACCAGTCGCTATAGTGAGTCGT-ATTA-3' (SEQ ID NO:9); Aptamer 23 was derived from a sense oligonucleotide 5'-TAATACGACTCACTATAACGTATCCCTTTTCG CGTA-3' (SEQ ID NO:10) and an antisense oligonucleotide, 5'-TACGCGAAAAGGGATACGT-3' (SEQ ID NO:11) (T7 RNA promoter sequence is underlined). Each pair of oligonucleotides was mixed in equal molar ratios in 1×PEI buffer (0.1 M Tris-HCl pH 8, 0.1 M MgCl$_2$ 0.5 M NaCl and 0.1 M dithiothreitol), heated for 5 min at 90° C. and cooled slowly to room temperature prior to ethanol precipitation. In vitro transcription and FITC-labelling was performed as described above. The final truncation of this clone (EpDT3), a fluoropyrimidine version of 5'-GCGACUGGUUCCCG-GUCGdT-3' (SEQ ID NO: 12) was also chemically synthesized with a 5'-DY647 fluorescent tag and a 3'-inverted deoxythymidine (Dharmacon). The binding affinity of DY647-EpDT3 was determined as described herein, using EpCAM-positive and -negative cell lines and a negative control (2-O-methyl-pyrimidine) aptamer (5'-DY647-mGC-mGACUmGmGUUmACCCmGmGUCmGdT-3') (SEQ ID NO:13).

Determination of Aptamer Affinity

The equilibrium dissociation constant (K'd) of successful 2'-fluoropyrimidine RNA aptamer species to native EpCAM expressed on the cell surface was determined using flow cytometry with EpCAM-positive and -negative cell lines and a negative control (2-O-methyl-pyrimidine) aptamer (5'-DY647-mGCmGACUmGmGUUmACCCmGmGUC-mGdT-3') (SEQ ID NO:13). Kato III or U118MG cells (5×10$^5$) were first incubated with assay buffer followed by two washes with binding buffer prior to incubation with serial concentrations (approximately 10-fold above and below the apparent K'd) of FITC-labelled aptamer in a 100 μL assay buffer for 1 h on ice. The cells were washed three times, resuspended in 150 μL assay buffer containing 2.5 mM MgCl$_2$ and subjected to flow cytometric analyses. The FITC-labelled unselected library was used as another negative control. The mean fluorescence intensity (MFI) of the unselected library was subtracted from that of the aptamer-target cell to generate the MFI of specific binding. The K'd for each aptamer was determined by Scatchard analysis according to the equation:

$$[\text{Bound aptamer}]/[\text{aptamer}] = -(1/K_D) \times [\text{bound aptamer}] + ([T]_{tot}/K_D)$$

where $[T]_{tot}$ represents the total target concentration.

Design and Generation of EpCAM Aptamer-siRNA Chimera

Two RNA strands were syntheses and the long strand was chemically modified with 2'-fluoropyrimidines. In the long strand, the 19nt EpCAM aptamer was covalently combined with the guide strand of survivin siRNA (Carvalho A et al. (2003) J Cell Science 116:2987-2998) through a two amino acid bridge, while the passenger strand of Survivin siRNA was synthesised as the short strand. Both the long strand (A) and short strand (B) have unstable secondary structures with free energy −7.5 kcal/mol and −0.5 kcal/mol for 43nt and 21nt, respectively. In contrast, theoretically, after annealing, the expected chimera has a much more stable structure with a free energy of −42.6 kcal/mol for 64nt. This means that after annealing, these two separated strands are more likely to create the expected aptamer-siRNA chimera (C). Furthermore, a 2 nt (UU) 3' overhang will be created after annealing, which will facilitate Dicer enzyme digestion of the chimera from 3' end of the guide strand of siRNA and finally result in the expected 21 mer siRNA. A fluorescent molecule (DY647) was added at the 5' end of the short strand, which not only facilitates image analysis, but also contributes to the structure symmetry of the chimera and results in expected siRNA after Dicer processing.

Example 1

Immunohistochemistry Using Chemical Antibodies

Figure 1:
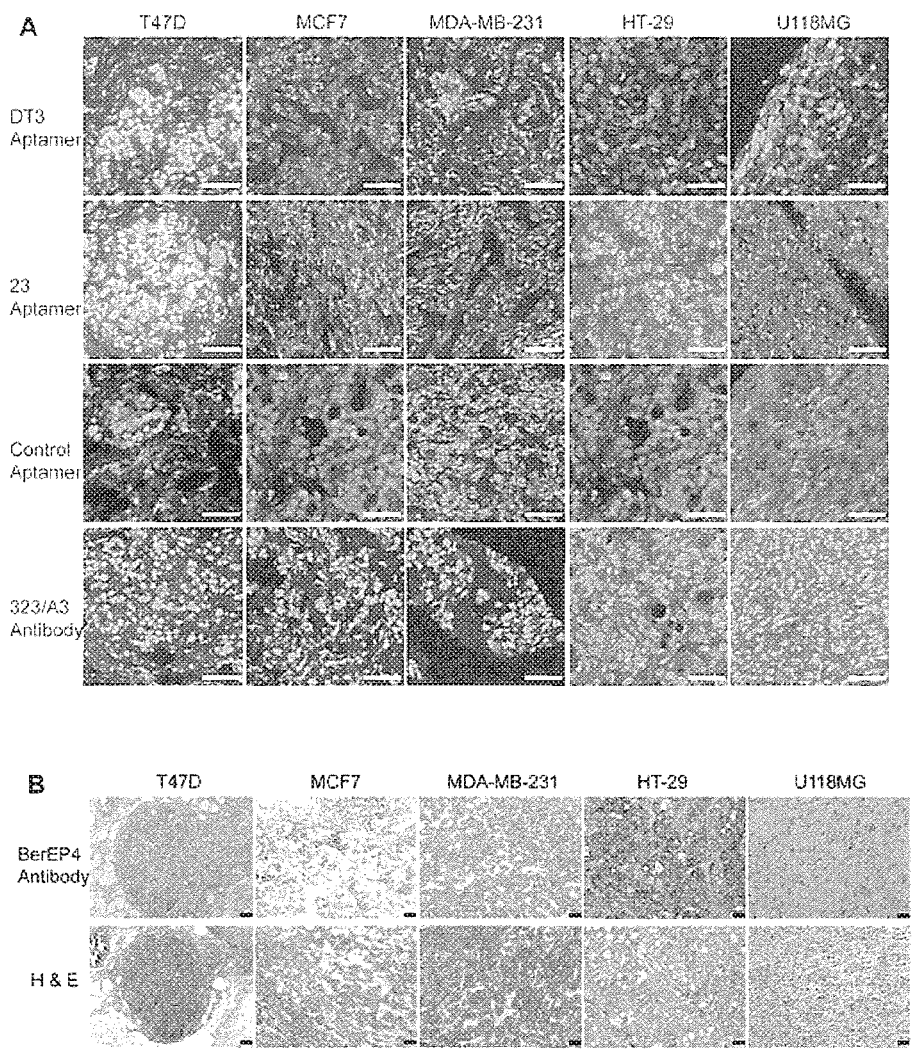
FIG. 1. Detection of EpCAM in paraffin embedded tissue using aptamers and antibodies.

When incubated in the presence of dextran sulphate and heparin, the anti-EpCAM aptamers DT3 and 23 showed highly sensitive staining of T47D, MCF7 and MDA-MB-231 human breast cancer xenografts at a concentration of 100 nM for 15 min at 37° C. (FIG. 1). Indeed, the staining pattern correlates well with the level of EpCAM expression seen on the surface of breast cancer cells, as demonstrated by weaker staining of the MDA-MB-231 xenograft sections that express much lower amounts of EpCAM than T47D and MCF7. As well, staining was shown to be highly specific, with no staining detectable for the U118MG xenograft that does not express EpCAM, nor staining with the control aptamer on any of the xenograft sections. During the optimisation process, the antigen retrieval methods were tested against those previously successfully utilised with the only other aptamer known to stain paraffin embedded tissue (Zeng Z et al (2010). Mod Pathol 23:1553-1558), as well as other antigen retrieval methods, such as enzyme digestion. While Zeng and colleagues showed successful aptamer staining with antigen retrieval performed at 37° C. (Zeng Z et al, supra), the present results did not concur. Instead, the inventors found that antigen retrieval performed at 96-100 CC for 20 mins to be highly effective for sensitive and specific staining.

It is interesting to note the dramatically different staining that was achieved with the HT-29 xenograft sections by the two EpCAM aptamers (FIG. 1). The binding affinities of both aptamers have been characterised against all five cell lines used in this study by flow cytometry, and the results are shown in Table 1.

TABLE 1

Binding affinities of EpCAM aptamers

| Cell Line | $K_D$ DT3 (±SEM) | $K_D$ 23 (±SEM) | $K_D$ Control (±SEM) |
|---|---|---|---|
| T47D | 74.2 ± 26.2 nM | 41.2 ± 29.2 nM | >1000 nM |
| MCF7 | 50.0 ± 18.5 nM | 63.7 ± 40.4 nM | >1000 nM |
| MDA-MB-231 | 98.9 ± 37.8 nM | 86.7 ± 68.5 nM | >1000 nM |
| HT29 | 158.0 ± 70.0 nM | 37.0 ± 23.6 nM | 837 ± 265 nM |
| U118MG | >1000 nM | >1000 nM | >1000 nM |

The different affinities for these cell lines would indicate that both aptamers recognise different portions of the EpCAM molecule. It is plausible that the discrepancy in reactivity results from the epitope that aptamer DT3 binds to becoming lost or remaining inaccessible following antigen retrieval.

Example 2

Aptamers are More Sensitive at Detecting EpCAM than Antibodies

As shown in FIG. 1 and Table 2, the intensity of antibody staining for the three different breast cancer xenografts using an anti-EpCAM antibody 323/A3 is much weaker than that of the aptamers, in particular aptamer 23. However, antibody 323/A3 did show moderate to strong staining of the HT-29 colorectal cancer xenograft. To exclude the possibility of the limitation of the protocols for fluorescent staining used within their laboratory, the inventors consulted a clinical pathology laboratory to confirm their results. The standard EpCAM stain in use at that laboratory is the anti-EpCAM antibody BerEP4. Following the routine protocol for this antibody used in pathology diagnostic practice, the inventors obtained similar staining of all xenograft tumours to those achieved using the 323/A3 antibody, indicating that the present aptamers are much more sensitive than the standard antibodies in use in pathology

TABLE 2

Quantification of anti-EpCAM staining in cell line xenografts using DT3, 23 and control aptamers and 323/A3 antibody by immunofluorescence and immunohistochemistry using BerEP4 antibody

| | Cell Lines | | | | |
|---|---|---|---|---|---|
| | T47D | MCF7 | MDA-MB-231 | HT-29 | U118MG |
| DT3 Aptamer | ++ | + | + | − | − |
| 23 Aptamer | +++ | ++ | + | +++ | − |
| Control Aptamer | − | − | − | − | − |
| 323/A3 Antibody | + | + | − | ++/+++ | − |
| BerEP4 Antibody | − | + | − | +++ | − |

'−' no staining;
'+' faint incomplete staining in >10% of cells;
'++' moderate complete membrance staining;
'+++' strong complete membrance staining.

Example 3

Detection of EpCAM at Low Levels of Expression

Among all the human cancer cell lines studied here, MDA-MB-231 cells express the lowest amounts of EpCAM ($1.7 \times 10^3$ binding sites/cell in MBD-MB-231 vs $222.1 \times 10^3$ binding sites/cell in MCF7 (Prang N et al (2005). Br J Cancer 92:342-349). Interestingly, both of the two aptamers (DT3 and 23) were able to successfully detect EpCAM in a xenograft tumour of MDA-MB-231, while the two antibodies showed negligible staining of this breast cancer xenograft (FIG. 1). In fact, using antibody staining, the MDA-MB-231 cells have previously been reported to have such a low level of expression of EpCAM as to be classed as EpCAM-negative (Prang N et al, supra), in both flow cytometry or immunohistochemistry studies (Keller P J et al (2010) Breast Cancer Res 12:R87). In contrast, the present inventors demonstrate here that RNA aptamers, at a comparable concentration, can reliably detect low levels of EpCAM in tumours the antibodies fail to do so. These results suggest promising potential of these aptamers for future diagnostic applications.

Example 4

EpCAM Aptamer-siRNA Chimera

Following confirmation of the efficacy of survivin siRNA and previous results showing the moderate binding affinity of the EpCAM aptamer, the inventors designed the first aptamer-siRNA chimera using EpCAM aptamer and survivin siRNA (FIG. 2). The secondary structures of these two RNA strands were predicted using "Nupack" (http://www.nupack.org).

Example 5

Aptamer-siRNA Chimera Created after Annealing

To confirm the successful annealing of both the long and short strands to create the expected aptamer-siRNA chimera (95° C. for 5 min), a native high definition agarose gel (4%) was used. As can been seen from FIG. 3, a distinct band was observed for the chimera, indicating a stable chimera structure has been created through annealing, which confirms prior structure analysis (FIG. 2).

Example 6

EpCAM Aptamer-siRNA Chimera Binds and Internalises within an EpCAM Positive Cancer Cell Line In Vitro FIG. 4 shows that the conjugation of siRNA to aptamer did not have an effect on the internalising capability of the aptamer. These results, together with a lack of non-specific binding, as indicated by no internalisation with the EpCAM-negative cell line, HEK-293T, shows that this complex should act as an efficient delivery molecule for siRNA to EpCAM-positive cell lines.

Example 7

EpCAM Aptamer-siRNA Chimera Targets Tumors Expressing EpCAM In Vivo

As shown in FIG. 5, after injection, the EpCAM aptamer-siRNA chimera could concentrate specifically in the tumour and that this result could be detected consecutively within four hours, with the peak present at about the time point of one hour. When tumour and organs were dissected and measured in vitro, fluorescence from aptamer-siRNA chimera still could be detected from the tumour and with a higher intensity than heart, liver, spleen and lung. The high fluorescence signal in the kidney probably resulted from the relatively larger blood flow volume and the small volume of chimera (about 4 nm and could be partly diffused through blood vessels). Theoretically, through further modification such as PEGylation and lull chemical modification, better plasma stability and lower kidney and liver accumulation could be achieved.

Example 8

Chimera can be Recognised by Dicer Enzyme after Internalisation

The ability of the EpCAM aptamer-survivin siRNA chimera (64 nt RNA oligonucleotide) to inhibit expression of survivin protein was compared with control survivin siRNA (the longer strand of the chimera without the passenger strand that was marked in green in FIG. 2C). The results shown in FIG. 6 indicates that the chimera was successfully processed by the Dicer enzyme once delivered to the cytoplasm to produce the 21-mer siRNA in cells. Indeed, as shown in FIG. 7, in an in vitro Dicer digestion analysis, the aptamer-siRNA chimera was successfully cleaved by the recombinant Dicer enzyme to produce the properly processed 21-mer siRNA.

Example 9

Chimera Demonstrates Gene Silencing Capability In Vitro

As can be seen from FIG. 6, after 24 hours incubation with the chimera without transfection reagent, the EpCAM aptamer-survivin siRNA chimera demonstrated gene silencing capability with both 20 nM and 100 nM doses (58.4% and 79.8% respectively). This suggested that this chimera can not only target EpCAM positive cells in both cell culture and in the animal body (FIG. 4 and FIG. 5), but also results in in vitro gene silencing without requiring a transfection reagent.

Example 10

EpCAM Aptamer Penetrates Tumour Sphere Much Better than Anti-EpCAM Antibody In Vitro To study the ability of EpCAM aptamer or antibody to penetrate tumors, the inventors used a three-dimensional in vitro tumor sphere model. Human colinic adenocarcinoma cell HT-29 that express high levels of EpCAM and human kidney cell HEK293 that does not express EpCAM were cultured in stem cell culture medium (DMEM/F12 with 20 ng/ml EGF and FGF and B27). When tumour sphere reached a size of ~300-400 µm, the sphere were incubated with 100 nM PE-labelled anti-EpCAM antibody, DY647-labelled EpCAM aptamer-23 or a DY647-labelled control aptamer that does not bind to EpCAM. After incubating for the indicated time, the spheres were washed twice with PBS and imaged via fluorescence confocal microscopy. A phase contrast image of the sphere was also taken for each sample. FIG. 8 shows the EpCAM antibody could only penetrate a few layers of cells on the surface of the tumor sphere even after 4 h. In sharp contrast, the EpCAM aptamer-23 could penetrate into the core or center of the tumor sphere at after 30 min incubation; while a control aptamer that does not bind to EpCAM showed only limited non-specific binding to the tumor sphere. A retention study was performed whereby the tumour spheres were incubated with EpCAM antibody, aptamer-23 or control aptamer for 4 h, after washing with PBS twice, the tumor spheres were incubated with the culture medium for a further 24 h followed by confocal microscopy. As shown in FIG. 9, there was no detectable fluorescence for EpCAM antibody. There was a very weak signal (close to background noise) for control aptamer. Conversely, there were clearly detectable signal for aptamer-23 throughout the entire tumor sphere. This demonstrates that aptamer-23 is not only able to penetrate into the core of the tumor sphere, but it is also retained by the tumor cells for at least 24 hours, most likely due to it efficient internalisation. The specificity and selectivity of EpCAM targeting was further demonstrated by data shown in Figure. 10, in which aptamer-23 showed minimal binding to the HEK293T sphere that does not express EpCAM.

Part 1 Examples 11 to 14. EpCAM Aptamer-Guided Delivery of a Chemotherapy Drug Transforms an Agent Known to Kill Only Non-Cancer Stem Cell into an Agent that Kills Cancer Stem Cells Both In Vitro and In Vivo.

Example 11

Aptamer23-Dox Conjugates, but not Free Dox, Target Cancer Stem Cells In Vitro Under non-adherent and serum-free conditions, only the cancer stem cells (CSCs) and progenitor cells survive and undergo self-renewal as well as proliferate to form tumour spheres. The inventor studied the ability of aptamer-Dox to target cancer stem cells by plating various cell doses of single-cell suspension of HT29 colon cancer cells in ultra-low attachment 96-wells in the presence of 3 µM of free Dox, 3 µM equivalent Dox conjugated with aptamer, 3 µM Dox-negative control aptamer or vehicle control for 5 days.

Tumour spheres (with a size >50 μm) were enumerated. Consistent with previous findings from both clinical and preclinical studies that Dox kills only non-CSCs, 3 μM free Dox had no effect on HT29 tumour sphere formation (Table 3).

TABLE 3

Tumourshpere formation in 96-well

| Cell line | No. cells seeded/ well | Vehicle control | Free Dox | Apt-Dox | Ctrl Apt-Dox | Saline |
|---|---|---|---|---|---|---|
| HT29 | 200 | 10/10 | 10/10 | 6/10 | 10/10 | 2/10 |
|  | 100 | 10/10 | 10/10 | 4/10 | 9/10 | 0/10 |
|  | 10 | 10/10 | 10/10 | 0/10 | 8/10 | 0/10 |
|  | 1 | 0/10 | 0/10 | 0/10 | 0/10 | 0/10 |
| PLC/ PRF/5 | 200 | 10/10 | 10/10 | 6/10 | 10/10 | 0/10 |
|  | 100 | 10/10 | 10/10 | 5/10 | 9/10 | 0/10 |
|  | 10 | 10/10 | 10/10 | 2/10 | 8/10 | 0/10 |
|  | 1 | 0/10 | 0/10 | 0/10 | 0/10 | 0/10 |

In contrast, 3 μM Dox conjugated with the EpCAM aptamer significantly reduced the tumour sphere numbers. Dox conjugated with the control aptamer had only a marginal effect on sphere formation, probably due to non-specific uptake by the cells. Salinomycin (Sal), known to target CSC[23], was used as a positive control to validate our assays. Furthermore, the inventor confirmed that the inhibition of HT29 tumour sphere formation by aptamer-Dox is not restricted to one specific tumour cell line as similar results were obtained using a hepatocellular carcinoma cell line (PLC/PRF/5) in which EpCAM has been shown to be a liver CSC marker (Table 3, bottom). We further confirmed the initial results by employing an ultra-low attachment 6-well format assay that uses a very different system for enumeration of spheres as well as serial passage of spheres to better assess the self-renewal capacity (data not shown). The final indication that aptamer-Dox treatment targets CSC in vitro came from FACS analysis of established CSC markers in HT29, EpCAM$^{high}$/CD44$^{high}$/CD24$^{high}$. As shown in FIG. 11B, in HT29 spheres treated with aptamer-Dox, there was only 0.52% EpCAM$^{high}$/CD44$^{high}$/CD24$^{high}$ cells, in sharp contrast to 91% of that in free Dox group (FIG. 11A) or 92.1% in the control aptamer-Dox group, respectively.

Example 12

EpCAM Aptamer-Dox Targets Cancer Stem Cells Ex Vivo

As sphere formation is a surrogate assay for in vivo tumourigenicity, the inventor examined whether the in vitro treated cells could generate tumours upon xenotransplantation. HT29 cells were treated with 3 μM free Dox or aptamer-Dox for 5 days and 1×10$^4$ or 1×10$^5$ treated cells (mixed with Matrigel) were injected subcutaneously into NOD/SCID mice (n=5). As shown in FIG. 12 and Table 4, free Dox-treated cells formed tumours in every mouse studied but no tumour was detected in mice cells (Table 4) at Day 50 after receiving aptamer-Dox-treated tumour implantation.

TABLE 4

Evaluation of tumour formation ex vivo

| No. cells injected | No. tumour/No. mice | | |
|---|---|---|---|
|  | Vehicle control | Free Dox | Apt-Dox |
| 1 × 10$^6$ | 5/5 | 5/5 | 0/5 |
| 1 × 10$^5$ | 5/5 | 5/5 | 0/5 |

Example 13

EpCAM Aptamer-Dox Targets Colon CSC In Vivo

The inventor first studied whether the aptamer-Dox conjugate could efficiently target tumour in vivo via live animal imaging with an on-site IVIS Lumina II imaging station. As shown in FIG. 13, the Dy647-labelled aptamer-Dox accumulated in the HT-29 xenograft tumour (s.c. approx. 5 mm in size) 5 min after i.v. injection and the signal in the tumour lasted for ~2 h. The ability of aptamer-Dox to target CSC was further tested in vivo using the gold standard extreme limiting dilution/xenotransplantation assay (ELDA). To this end, the inventor injected 1×10$^6$ HT29 cells s.c. into NOD/SCID mice. When tumours reached a size of 3 mm, the mice were randomized and treated serially for 3 days at a daily dose of 5 mg/Kg of either free Dox, EpCAM aptamer-Dox or control aptamer-Dox via tail vein injection. Mice were sacrificed one week after the last treatment. As shown in FIG. 14, after only 3 injections, the tumours from aptamer-Dox treated groups were statistically significantly smaller/lighter than mice receiving free Dox or Dox conjugated with the control aptamer. The experiment as repeated and single cell suspensions prepared from the treated tumours (as in FIG. 14) and ELDA (Extreme limiting dilution analysis) performed to assess the effect on CSC frequency. As shown in Table 5, EpCAM aptamer-Dox conjugates were able to significantly reduce the tumourigenicity in vivo as determined at 9 weeks alter inoculation.

TABLE 5

Tumourigenicity of HT29 cell populations

| No. cells injected | No. tumour/No. mice | | |
|---|---|---|---|
|  | Control Apt-Dox | Free Dox | Apt-Dox |
| 1 × 106 | 6/6 | 6/6 | 2/6 |
| 1 × 105 | 6/6 | 6/6 | 1/6 |
| 1 × 104 | 0/6 | 0/6 | 0/6 |

Example 14

Conjugation of a 20 kDa-PEG to the 5'-End of EpCAM Aptamers Improves its Biodistribution and Tumour Targeting PEG-aptamer-Dox (5 mg Dox/kg) was injected i.v. to tumour bearing-mice. The percentage (%) ID of PEG-aptamer normalised by the weight of a given tissue/organ (in g) as determined via aptamer ELISA is plotted in the bar chart shown in FIG. 15.

Taken together, the data from Examples 11 to 14 show that EpCAM-23-directed RNA aptamer-doxorubicin conjugates are able to target cancer stem cells both in vitro and in vivo.

Part 2 Examples 15 to 17. EpCAM Aptamer-Guided Delivery of siRNA Overcomes Chemoresistance Via Effective Targeting of Cancer Stem Cell In Vivo.

Example 15

EpCAM Aptamer-Mediated siRNA Delivery Targets Cancer Stem Cells In Vitro

Doxorubicin (Dox), on its own, does not kill cancer stem cells. The inventor hypothesized that the CSC-targeted delivery of survivin siRNA would make CSC sensitive to Dox. Indeed, after treatment (without transfection reagent) with 20 nM chimera plus 300 nM Dox for 72 h, there was a ~80% reduction in the number of mammospheres in both the first and second round of tumoursphere assays (not shown), indicating a significant portion of cancer stem cells had been eliminated. The inventor further confirmed the effect of the chimera plus Dox on cancer stem cells' tumourigenicity by xenotransplanting treated cells into the 4th inguinal mammary fat pads of NOD/SCID mice coupled with an extreme limiting dilution analysis to assess CSC frequency (at Day 40 alter implantation) (Table 6). Finally, as shown in FIG. 16, treatment of tumourspheres in vitro with chimera plus 300 nM Dox resulted in a significant decrease of breast cancer CSCs (EpCAM$^+$ CD44$^+$/CD24$^-$) than that of free Dox alone (FIG. 16), while the EpCAM$^+$/CD44$^+$/CD24$^-$ population remained at ~22.5% and 21.7% for cells treated with vehicle control or negative control chimera plus Dox, respectively. These results establish that EpCAM aptamer-survivin siRNA chimeras target cancer stem cells in the MCF7/ADR breast carcinoma drug resistance model in vitro.

TABLE 6

Tumourigencicity ex vivo

| Treatment | No. of cells injected | No. of tumours/no. of mice |
|---|---|---|
| Vehicle control | $5 \times 10^6$ | 5/5 |
| | $3 \times 10^6$ | 4/5 |
| | $1 \times 10^6$ | 1/5 |
| | $0.5 \times 10^6$ | 0/5 |
| 300 nM Dox only | $5 \times 10^6$ | 5/5 |
| | $3 \times 10^6$ | 3/5 |
| | $1 \times 10^6$ | 1/5 |
| | $0.5 \times 10^6$ | 0/5 |
| 20 nM control chimera + 300 nM Dox | $5 \times 10^6$ | 7/7 |
| | $3 \times 10^6$ | 5/7 |
| | $1 \times 10^6$ | 1/7 |
| | $0.5 \times 10^6$ | 0/7 |
| 20 nM Chimera + 300 nM Dox | $5 \times 10^6$ | 2/7 |
| | $3 \times 10^6$ | 0/7 |
| | $1 \times 10^6$ | 0/7 |
| | $0.5 \times 10^6$ | 0/7 |

Example 16

EpCAM Aptamer Delivers siRNA to Xenograft Tumour In Vivo and Targets Cancer Stem Cells An orthotopic breast cancer model was established by implanting $3 \times 10^6$ MCF7/ADR cells (mixed with Matrigel) per site in NOD-SCID mice. When tumours reached a volume of ~200 mm$^3$, we started treatment via tail vein injection. The mice (n=5) were treated at Day 1, 3, 5, with i.v. (bolus) injection of 1 nmole of EpCAM aptamer-siRNA chimera; and Day 2, 4, 6, with i.v. (bolus) injection of 5 mg/kg doxorubicin. The animals were euthanized on Day 10 and tumours harvested and subjected to xenotransplantation and in vivo extreme limiting dilution analysis. As shown in FIG. 17, the in vivo efficacy of the chimera (without PEG) was demonstrated by its ability to knockdown both the survivin mRNA and protein by ~60%. Importantly, the EpCAM-targeted delivery of survivin siRNA combined with treatment of Dox had eliminated a substantial portion of the cancer stem cells in the MCF7/ADR tumour in vivo as evident from the xenotransplantation-extreme limiting dilution analyses that assess the distinguishing features of cancer stem cells, self-renew and tumourigenicity of the tumours (at Day 50 after implantation) (Table 7).

TABLE 7

Xenotransplantation-LDA

| Treatment | No. of cells injected | No. of tumours/no. of mice |
|---|---|---|
| Vehicle control | $5 \times 10^6$ | 4/4 |
| | $3 \times 10^6$ | 3/4 |
| | $1 \times 10^6$ | 1/4 |
| | $0.5 \times 10^6$ | 0/4 |
| 5 mg/kg Dox only | $5 \times 10^6$ | 4/4 |
| | $3 \times 10^6$ | 3/4 |
| | $1 \times 10^6$ | 1/4 |
| | $0.5 \times 10^6$ | 0/4 |
| control chimera + 5 mg/kg Dox | $5 \times 10^6$ | 4/4 |
| | $3 \times 10^6$ | 3/4 |
| | $1 \times 10^6$ | 1/4 |
| | $0.5 \times 10^6$ | 0/4 |
| 1 nmole Chimera + 5 mg/kg Dox | $5 \times 10^6$ | 2/4 |
| | $3 \times 10^6$ | 1/4 |
| | $1 \times 10^6$ | 0/4 |
| | $0.5 \times 10^6$ | 0/4 |

Example 17

Improvement of Pharmacokinetics of EpCAM-siRNA Chimera Further Enhances Treatment Efficacy A 20-kDa PEG was attached to the 5'-end of siRNA-aptamer-chimera in order to extend its systemic circulation time. The inventor then used the same orthotopic breast cancer model by implanting $3 \times 10^6$ MCF7/ADR cells (mixed with Matrigel) per site. When tumours reached a volume of ~200 mm$^3$, we started treatment. The mice (n=8) were treated at Day 1, 3, 5, with i.v. (bolus) injection of 1 nmole of EpCAM aptamer-siRNA chimera; and Day 2, 4, 6, with i.v. (bolus) injection of 5 mg/kg doxorubicin. Day 2 after the last (third) treatment, tumours were removed, its weight determined and the percentage of breast cancer stem cell marker (EpCAM$^+$/CD44$^+$/CD24$^-$) positive cells in the treatment groups and various control groups was studied via flow cytometray. As shown in FIG. 18, the tumours from the mice treated with EpCAM-23 aptamer-survivin siRNA chimera plus doxorubicin had significantly reduced tumour total tumour mass (weight) than that of any of the other treatment groups, including the group treated with free doxorubicin. Furthermore, judging from the proportion of breast cancer stem cell marker-positive cells, the treatment by EpCAM-23 aptamer-survivin siRNA chimera plus doxorubicin has drastically reduced the breast cancer stem cell pool (Table 8).

Taken together, EpCAM-23 aptamer-guided delivery of siRNA to cancer stem cell in vivo enhances treatment efficacy by preventing the development of chemoresistance.

TABLE 8

CSCmarker status in various treatment groups

| Percentage EpCAM+/ CD44+/ CD24− | Saline | Free Dox | Control Apt | Control Apt + Dox | Chimera only | Chimera + Dox |
|---|---|---|---|---|---|---|
| | 11.8 ± 0.6 | 11.6 ± 0.5 | 12.8 ± 0.7 | 11.9 ± 0.4 | 7.8 ± 0.3 | 1.8 ± 0.05 |

MCF-7/ADR tumours (0.2 mm$^3$) were treated 3 times in a week with 1 nmol PEG-chimera+5 mg/kg doxorubicin. Single cell suspension was prepared for flow cytometry (n=8).

Remarks

A sensitive and reliable method for detecting the expression of cancer biomarker proteins in histopathology sections is essential for personalised medicine that is based on the molecular information underlying the lesions. EpCAM is a cancer biomarker with its overexpression documented in both primary and metastatic breast cancers. The adverse clinical outcomes of such patients are associated with increasing EpCAM expression especially in the metastases. In addition, a poorer prognosis in gallbladder, ovarian and pancreatic cancer has also been associated with an overexpression of EpCAM. Indeed, it has been suggested that EpCAM expression in triple-negative breast cancers may be a suitable target for immunotherapy, given its resistance to current targeted therapies, such as endocrine treatment and trastuzumab. In a study using a fully humanised monoclonal anti-EpCAM antibody, adecatumumab (MT201), patients with metastatic breast cancer showed dose-dependent and target dependent clinical responses with a reduced rate of new metastases.

Following immunohistochemical studies and the results from several EpCAM immunotherapy clinical trials, it has been suggested that the level of EpCAM expression be tested for in cancer patients, given the increased use of immunotherapy and the use of anti-EpCAM antibodies for the treatment of tumours that express high levels of EpCAM. Indeed, it has even been suggested that the failure of some clinical trials of anti-EpCAM immunotherapy could be related to the lack of prior knowledge of EpCAM expression in the tumours to be treated. Here the present inventors demonstrate that aptamers are particularly suitable for, and superior to antibodies for histological diagnosis. While extensive optimisation was required in the attempt to use these aptamers as chemical antibodies, the realisation that these probes are nucleic acids and therefore might require a combinational approach of both conventional antibody staining, along with similar methods used for in situ hybridisation, proved to be highly successful. The use of dextran sulphate has been shown to accelerate the rate of nucleic acid hybridisation thus reducing the time required for aptamer incubation, while heparin has been shown to reduce background binding in hybridisation procedures. When either of these two reagents was omitted from the hybridisation buffer, positive staining was not achieved, even when the incubation time was increased. Indeed, this approach was successful for all the aptamers tested for EpCAM staining. We anticipate that this improved protocol will prove to be highly effective for the use of other aptamers in the staining of paraffin embedded tissues.

In this study, prior aptamer DT3 did not show any staining of HT-29 xenograft sections, while the other aptamer tested, aptamer 23, showed strong positive staining. One possibility is that the particular epitope that DT3 binds to on the EpCAM molecule may be lost or remains inaccessible due to other antigens on the cell surface masking that epitope on this particular tumour. However, given the positive reactivity seen in the three breast cancer xenografts, it is unlikely that a loss of epitope is responsible. Alternatively, this particular epitope remains masked on this xenograft tumour following antigen retrieval. As well, the lower affinity that aptamer DT3 has for this cell line might also play a role and it could be a combination of these two factors that lead to a lack of immunostaining.

The sharp contrast between the ability of the present aptamer in detecting low levels of antigen in paraffin embedded tissues and the failure of the conventional antibodies tested to stain the same tumours is interesting. Aptamers are 10-20 times smaller (6 kDa vs 150 kDa) than antibodies and it is therefore possible that more numbers of aptamers bind to a given target molecule than antibodies. In addition, the smaller size of aptamer may facilitate it to penetrate the layers of cells in a histopathology slides more effectively. This could be one of the reasons why the inventors are able to detect EpCAM expression on the surface of MDA-MB-231 cells via aptamer staining of paraffin embedded tissues, when this cell line is generally regarded as EpCAM negative due to the inability of antibodies to detect its expression. Conceivably, low levels of EpCAM expression might be missed during diagnosis using conventional antibody staining.

This study has used xenograft tumours to characterise the present EpCAM aptamer as a histological reagent. One reason for this is due to the difficulty in obtaining appropriate human tissue. However, it has been proposed that the xenograft tumour largely recapitulates the histology of the tumour faithfully in vivo at least in the tumours studied by others. The histopathology of the xenograft tumours used in this study have been confirmed by pathologists. The results from this proof-of-principle study demonstrates that aptamers are not only capable of functioning as chemical antibodies but are also more sensitive than conventional antibodies at least with the EpCAM antibodies tested. Given aptamers can be readily chemically synthesised, this study paves the way for the application of these chemical antibodies in future histopathological diagnosis.

The present results suggest that aptamers can provide a robust and cost-effective tool to translate discoveries from biomarker and cancer stem cell research into pathology diagnostic practice to enable better stratification of patients for personalized medicine.

The claims defining the invention are as follows:

1. An RNA aptamer which binds specifically to EpCAM, wherein:
    the aptamer is not DT3 having the sequence GCGACUGGUUACCCGGUCG (SEQ ID No:1); and
    the aptamer comprises the sequence ACGUAUCCUUUUCGCGUA (SEQ ID No:2) or a sequence comprising one or more substitutions within the sequence of SEQ ID No:2.

2. The aptamer according to claim 1 wherein the aptamer comprises a sequence length between 19 and 100 bases.

3. The aptamer according to claim 1 wherein the aptamer comprises one or more modifications that increase aptamer stability.

4. The aptamer according to claim 1, which consists of the sequence of SEQ ID No:2.

5. The aptamer according to claim 1, wherein the aptamer specifically binds to EpCAM+ cancer stem cell(s).

6. The aptamer according to claim 5, wherein the cell is a breast cancer stem cell, a prostate cancer stem cell, a pancreatic cancer stem cell, a colon cancer stem cell, a liver cancer stem cell, a lung cancer stem cell, an ovarian cancer stem cell, or a head and neck cancer stem cell.

7. The aptamer according to claim 5, wherein the cell is present in a biological sample obtained from a subject.

8. A diagnostic agent comprising the RNA aptamer according to claim 1 coupled to a detectable label.

9. The diagnostic agent according to claim 8, wherein the detectable label is selected from an enzyme, prosthetic group, fluorescent material, luminescent material, bioluminescent material, electron dense label, labels for MRI and radioactive material and combinations thereof.

10. The aptamer according to claim 1, or a diagnostic agent comprising the aptamer of claim 1 coupled to a detectable label for use in histological examination of biological samples.

11. An anticancer agent comprising the RNA aptamer according to claim 1 coupled to a moiety.

12. The anticancer agent according to claim 11 wherein the moiety is selected from a toxin, a radionuclide, a chemotherapeutic agent and combinations thereof.

13. A method for isolating, purifying or enriching a EpCAM expressing cell(s) and/or cancer stem cell(s) from a biological sample obtained from a subject, the method comprising contacting the cell with an RNA aptamer according to claim 1 or a diagnostic agent comprising the aptamer of claim 1 coupled to a detectable label.

14. A method for identifying a EpCAM expressing cell(s) and/or cancer stem cell(s) in a subject or in a biological sample obtained from a subject having, or suspected of having cancer, the method comprising contacting the cell with an isolated RNA aptamer according to claim 1 or a diagnostic agent comprising the aptamer of claim 1 coupled to a detectable label.

15. The method according to claim 13, wherein the subject is one which has a cancer selected from breast cancer, prostate cancer, pancreatic cancer, colon cancer, liver cancer, lung cancer, ovarian cancer, head and neck cancer, melanoma or any other cancer in which EpCAM$^+$ cells are present.

16. The method according to claim 14, wherein the subject is one which has a cancer selected from breast cancer, prostate cancer, pancreatic cancer, colon cancer, liver cancer, lung cancer, ovarian cancer, head and neck cancer, melanoma or any other cancer in which EpCAM$^+$ cells are present.

17. A method for treating or preventing cancer in a subject comprising providing a subject with an RNA aptamer according to claim 1, or an anticancer agent comprising the RNA aptamer according to claim 1 coupled to a moiety.

18. A delivery agent comprising an RNA aptamer according to claim 1, coupled to an siRNA or ribozyme.

19. The delivery agent according to claim 18 comprising the sequence ACGUAUCCCUUUUCGCGUAAAAUGUAGAGAUGCGGUGGUCCUU (SEQ ID NO:3).

20. A composition comprising:
    one of:
        a therapeutically effective amount of an RNA aptamer comprising the sequence of SEQ ID No:2 wherein the aptamer binds specifically to EpCAM;
        an anticancer agent comprising the RNA aptamer coupled to a moiety; or a delivery agent comprising the RNA aptamer coupled to an siRNA or ribozyme;
and a pharmaceutically acceptable carrier and/or excipient.

21. The aptamer of claim 1, comprising at least one, two, three, four, five or six substitutions within the sequence of SEQ ID No:2.

22. The aptamer of claim 3, wherein the pyrimidine bases of the aptamer are 2'-fluoro (2'-F) modified.

23. The aptamer of claim 3, wherein the 3' end of the aptamer is modified to protect it from nuclease digestion.

24. The aptamer of claim 3, wherein the aptamer is modified by coupling the 5' end to a fluorophore, inverted dT or a PEG molecule.

* * * * *